(12) United States Patent
Sasaki et al.

(10) Patent No.: US 7,692,030 B2
(45) Date of Patent: Apr. 6, 2010

(54) CONJUGATES OF ARTEMISININ-RELATED ENDOPEROXIDES AND HYDRAZONE DERIVATIVES FOR THE TREATMENT OF CANCER

(75) Inventors: Tomikazu Sasaki, Bothell, WA (US); Henry Lai, Seattle, WA (US); Narendra P. Singh, Lynnwood, WA (US)

(73) Assignee: University of Washington, Seattle, WA (US)

( * ) Notice: Subject to any disclaimer, the term of this patent is extended or adjusted under 35 U.S.C. 154(b) by 221 days.

(21) Appl. No.: 11/872,651

(22) Filed: Oct. 15, 2007

(65) Prior Publication Data

US 2008/0103192 A1 May 1, 2008

Related U.S. Application Data

(60) Provisional application No. 60/851,489, filed on Oct. 13, 2006.

(51) Int. Cl.
*C07D 323/00* (2006.01)
*A01N 43/02* (2006.01)

(52) U.S. Cl. ...................................... 549/349; 514/450
(58) Field of Classification Search ................. 549/349; 514/450
See application file for complete search history.

(56) References Cited

U.S. PATENT DOCUMENTS

| 5,225,427 | A | 7/1993 | Venugopalan |
| 5,578,637 | A | 11/1996 | Lai |
| 6,743,893 | B2 | 6/2004 | Engler |
| 2004/0058981 | A1 | 3/2004 | Lai |
| 2004/0067875 | A1 | 4/2004 | Lai |
| 2006/0142377 | A1 | 6/2006 | Posner |
| 2006/0193778 | A1 | 8/2006 | Engler |
| 2007/0231300 | A1 | 10/2007 | Sasaki |

FOREIGN PATENT DOCUMENTS

| WO | WO03/000676 A1 | 1/2003 |
| WO | WO2007/112451 A2 | 10/2007 |

OTHER PUBLICATIONS

Delhaes, L., et al., "Novel Ferrocenic Artemisinin Derivatives: Synthesis, In Vitro Antimalarial Activity and Affinity of Binding with Ferroprotoporphyrin IX," Bioorganic & Medicinal Chemistry 8:2739-2745, 2000.
Kamchonwongpaisan, S., et al., Mechanism-Based Development of New Antimalarials: Synthesis of Derivatives of Artemisinin Attached to Iron Chelators, Journal of Medicinal Chemistry 38(13):2311-2316, 1995.
Posner, G.H., et al., "Structure-Activity Relationships of Lactone Ring-Opened Analogs of the Antimalarial 1,2,4-Trioxane Artemisinin," Journal of Medicinal Chemistry 38(4):607-612, 1995.
Wang, D.-Y., et al., "Synthesis, Iron(II)-Induced Cleavage and In Vivo Antimalarial Efficacy of 10-(2-hydroxy-1-naphthyl)-deoxoqinghaosu(-deoxoartemisinin)," Journal of the Chemical Society, Perkin Transactions 1:1827-1831, 1999.
Dong, Y., et al, "Effect of Functional Group Polarity on the Antimalarial Activity of Spiro and Dispiro-1,3,4-trioxolanes," Bioorganic & Medicinal Chemistry 14(6) 6368-6382, 2006.

*Primary Examiner*—D. Margaret Seaman
*Assistant Examiner*—Nizal S Chandrakumar
(74) *Attorney, Agent, or Firm*—Christensen O'Connor Johnson Kindness PLLC

(57) ABSTRACT

Compounds having an artemisinin-related endoperoxide moiety covalently coupled to a hydrazone moiety through a linker. Compositions and methods for treating cancer using the compounds.

19 Claims, 12 Drawing Sheets

CONJUGATES OF ARTEMISININ-RELATED ENDOPEROXIDES AND HYDRAZONE DERIVATIVES FOR THE TREATMENT OF CANCER

CROSS-REFERENCE TO RELATED APPLICATION

This application claims the benefit of Provisional Application No. 60/851,489, filed Oct. 13, 2006, the disclosure of which is hereby incorporated by reference.

BACKGROUND OF THE INVENTION

Artemisinin is a sesquiterpene lactone isolated from the plant *Artemisia annua* L, extracts, which has been used to treat malaria and a variety of other ailments for nearly 2000 years. Artemisinin and its derivatives, such as dihydroartemisinin, artemether, artesunate, arteether, propylcarbonate dihydroartemisinin, and artelinic acid, are most commonly known as potent anti-malarial agents. The artemisinin molecule contains an endoperoxide moiety, or oxygen bridge. The anti-malarial activity of artemisinin is due to the reaction between its endoperoxide bridge and intra-parasitic heme that generates free radicals, causing cell death.

The artemisinin molecule and related compounds have been studied extensively covering aspects such as characterization, total synthesis, and understanding of the mechanism of action through QSAR studies. These studies have unveiled a large amount of information about the artemisinin and related endoperoxide compounds and have resulted in a large number of published and patented literatures (See, Bez, G., et al., *Current Organic Chemistry* 7:1231-1255, 2003). For example, the endoperoxide function has been shown to be essential for the antimalarial activity of artemisinin (Gu, *Acta Pharmacol. Sinica* 1(1):48-50, 1980 Abstract). The total synthesis of (+)-artemisinin has been reported (Avery, M. A., et al., *Tetrahedron Letters* 28:4629-4632, 1987). The same group also synthesized several simplified analogues of artemisinin (Avery, 1987). Lin et al. reported a new series of hydrolytically stable and water-soluble dihydroartemisinin derivatives with optically active side chains as potential antimalarial agents (Lin, 1989). Imakura et al. reported the study of acid degradation products of artemisinin and their structure-activity relationships (Imakura, Y., et al., *Heterocycles* 31(6):1011-1016, Jun. 1, 1990. Abstract). Zaman et al. reported the aspects of the chemistry and biological activity of artemisinin and related antimalarials. (Zaman, S. S., and R. P. Sharma, *Heterocycles* 32:1593-1638, 1991). Peters et al. evaluated the activities of some synthetic artemisinin endoperoxide 1,2,4-trioxanes against several lines of *Plasmodium berghei* and *P. yoelii* ssp. in vivo (Peters, W., et al., *Ann. Trop. Med. Parasit.* 87(1):9-16, 1993). The results from these studies have enabled scientists during the 1990s to delineate the basic structural requirement for artemisinin-related endoperoxides—the 1,2,4-trioxane ring system—as the essential pharmacophore for artemisinin. Since then, interest in artemisinin has persisted. Benoit-Vical et al. reported the in vitro and in vivo potentiation of artemisinin and synthetic endoperoxide antimalarial drugs in 2000 (Benoit-Vical, F., et al., *Antimicrobial Agents and Chemotherapy* 44(10):2836-2841, 2000). Recently, Anfosso et al. used microarray expression profiles of angiogenesis-related genes to predict tumor cell response to artemisinin (Anfosso, L. et al., *Pharmacogenomics Journal*, 2006, pp. 1-10).

As a result of an apparent association between the endoperoxide functional group and antimalarial activity of artemisinin, a substantial effort has been devoted to developing new peroxide antimalarials (Vennerstrom, J. L., and J. W. Eaton, *Journal of Medicinal Chemistry* 31(7):1269-1277, 1988). Motivated by the structure and pharmacological mechanism of artemisinin, a large number of molecules containing the core pharmacophore, 1,2,4-trioxane, as well as its close analogue, 1,2,4,5-tetraoxane, and other endoperoxides have been synthesized and studied (U.S. Pat. No. 6,906,205, U.S. Pat. No. 6,486,199).

1,2,4-Trioxane itself has not been isolated or characterized. The tremendous amount of literature in the field suggests that it is the discovery of artemisinin with its novel 1,2,4-trioxane heterocyclic pharmacophore that initiated the development of 1,2,4-trioxanes, 1,2,4,5-tetraoxanes, and other artemisinin-related endoperoxides derivatives. Rational design of structurally simpler analogs of artemisinin has led to the synthesis of various racemic 1,2,4-trioxanes displaying potent antimalarial activities (U.S. Pat. No. 5,225,437). One group reported the development of dispiro-1,2,4,5-tetraoxanes as endoperoxide antimalarial drugs (Vennerstrom, J. L., et al., *Journal of Medicinal Chemistry* 35:3023-3027, 1992), as well as identification of a series of 1,2,4-trioxolane antimalarial drug candidates (US 2005/0256185).

Cancer cells have a significantly higher influx of iron than normal cells. Accordingly, it has been shown that artemisinin and artemisinin analogs are cytotoxic against established tumors and tumor cell lines (see, e.g., Woerdenbag, et al. (1993) *J. Nat. Prod.* 56(6):849-56; Lai and Singh (1995) *Cancer Lett.* 91:41-6; Efferth, et al. (2001) *Int. J. Oncol.* 18:767-73; Li, et al. (2001) *Bioorg. Med. Chem. Lett.* 11:5-8; Singh and Lai (2001) *Life Sci.* 70:49-56; Efferth, et al. (2002) *Biochem. Pharmacol.* 64:617-23; Efferth, et al. (2002) Blood Cells, Molecules and Diseases 28(2): 160-8; Sadava, et al. (2002) *Cancer Lett.* 179: 151-6; Singh and Lai (2004) *Anticancer Res.* 24(4):2277-80; Lai, et al. (2005) *Expert Opin Ther Targets.* 9(5):995-1007; Lai and Singh (2006) *Cancer Lett.* 231(1):43-8).

Similarly, artemisinin and its derivatives are also selectively cytotoxic to other cells with uncontrolled elevated free iron levels. Representative cells with elevated free iron level include cancer cells, pathogenic organisms, and abnormally hyperproliferating cells found in conditions, such as restenosis, arthritis, hyperplasia, and psoriasis (see, e.g., Golenser, et al. (2006) *Int. J. Parasitol.* 36(14):1427-41; Efferth, et al. (2002) *J. Mol. Med.* 80(4):233-42; Jung and Schinazi (1994) *Bioorg. Med. Chem. Lett. No.* 7; 931-934; Kaptein, et al. (2006) *Antiviral Res.* 69(2):60-9; Paeshuyse, et al. (2006) *Biochem. Biophys. Res. Commun.* 15; 348(1):139-44; Razavi, et al. (2007) *Int. J. Toxicol.* 26(4):373-80; Li, et al. (2006) *Int. Immunopharmacol.* 6(8):1243-50; Wang, et al. (2006) *Antimicrob. Agents Chemother.* 50(7):2420-7; Xu, et al. (2007) *Rheumatology* (Oxford)).

Iron chelators are small molecules that bind to iron metal ions. Iron is critical for proliferation of cells and vital cellular processes, such as oxygen transport, energy production and DNA synthesis, which are dependent on iron-containing proteins and enzymes. Therefore, iron chelators are expected to possess various biological activities. It has been demonstrated that iron chelators have anti-tumor activities. Iron chelators induce cytotoxic effects on tumors by starving them of iron or by inducing oxidative stress in the tumors through redox perturbations. A number of iron chelators have been tested for anti-tumor activity in microbiology studies, animal models and human clinical trials (see, e.g., Lee, et al. (2006) *J. Oral Pathol. Med.* 35(4):218-26; Hoke, et al. (2005) *Free Radic. Biol. Med.* 1; 39(3):403-11; Shen, et al. (2005) In Vivo. 2005 19(1):233-6; Buss, et al. (2004) *Curr. Top. Med. Chem.*

4(15):1623-35; Buss, et al. (2003) *Curr. Med. Chem.*10(12): 1021-34; Lovejoy and Richardson (2003) *Curr. Med. Chem.* 10(12):1035-49; Richardson (2002) *Crit. Rev. Oncol. Hematol.* 42(3):267-81).

The hydrazones constitute a class of iron-binding organic compounds, and certain members of the hydrazone class have been shown to inhibit cellular proliferation by removing iron from the active site of key enzymes, such as ribonucleoside reductase. In general, rapidly proliferating cancer cells are more sensitive to the hydrazones than the corresponding normal cells (see, e.g., Lovejoy, et al. (2006) *Hemoglobin.* 30(1): 93-104; Walcourt, et al. (2004) *Int. J. Biochem. Cell. Biol.* 36(3):401-7; Lovejoy and Richardson. (2003) *Curr. Med. Chem.* 10(12):1035-49; Becker, et al. (2003) *Br. J. Pharmacol.* 138(5):819-30; Chaston, et al. (2003) *Clin. Cancer. Res.* 9(1):402-14; Lovejoy and Richardson (2002) *Blood* 100(2): 666-76).

Attempts to combine artemisinin derivatives and iron chelators have been previously described in the literature to treat malaria, but have largely been therapeutically unsuccessful. For example, the synthesis of covalent conjugates between o-phenanthroline, a strong iron chelator, and an artemisinin-related endoperoxide for malaria therapy was reported in 1995 (Posner, et al. (1995) *J. Med. Chem.* 38(4): 607-12), but the studied conjugates and related compounds were not particularly active antimalarial agents in vitro. Another group reported the synthesis of a series of covalent conjugates between artemisinin and a variety of iron chelators, including hydroxamates and phenolates, for malaria therapy (Yuthavong et al. (1995) *J Med. Chem.* 38(13):2311-6). Again, these conjugates did not demonstrate enhanced antimalarial activities, compared to artemisinin alone. These studies suggest that the simple conjugation of an iron chelator to artemisinin does not necessarily produce more active cytotoxic compounds. More recently, another group reported the synthesis of artemisinin conjugates with naphthol, an iron-binding molecule, for malaria therapy (Wang, et al. (1999) *J. Chem. Soc. Perkin. Trans.* 1827-1832). Based on the antimalarial activities of two stereoisomers, it was suggested that the naphthol group might assist iron in binding to the endoperoxide group before the artemisinin moiety is activated. To date none of the artemisinin-iron chelator compounds described above has been tested for activity in cancer or non-malarial proliferative diseases in published literature.

U.S. Pat. No. 5,225,427 discloses 10-substituted ether derivatives of dihydroartemisinin alleged to exhibit antimalarial and antiprotozoal activity.

U.S. Pat. No. 5,578,637 discloses methods of killing cancer cells wherein compounds having an endoperoxide moiety that is reactive with heme are administered under conditions which enhance intracellular iron concentrations. Endoperoxide bearing sesquiterpene including artemisinin and its analogs are preferred compounds.

U.S. Patent Application No. 2004/0058981 discloses methods for preventing or delaying the development of cancer by administering free radical-generating agents to a subject. Preferred compounds include endoperoxide bearing sesquiterpene compounds such as artemisinin and its analogs. Intracellular iron concentrations may be enhanced by the administration of iron salts or complexes.

U.S. Patent Application No. 2004/0067875 discloses covalent conjugates between artemisinin-related endoperoxides and iron-carrying proteins, such as holotransferrin, to treat cancer and infections by pathogens that bind iron-carrying proteins.

U.S. Patent Application No. 2006/0193778 and U.S. Pat. No. 6,743,893 disclose peptides discovered by phage display techniques that are capable of binding to and internalizing with the human transferring receptor, including the peptides HAIYPRH (SEQ ID NO: 1) and THRPPMWSPVWP (SEQ ID NO: 2).

U.S. Patent Application No. 2006/0142377 discloses orally active artemisinin-derived trioxane dimers suitable as orally active compounds, which demonstrate antimalarial and anti-tumor activities.

U.S. Patent Application No. 2007/0231300 discloses covalent conjugates between artemisinin-related endoperoxides and small peptides and organic compounds that bind to molecular cavities on the transferrin or lactoferrin receptor, and the use of these conjugates to treat cancer, hyperproliferative disorders, inflammatory diseases, and infections.

There is a need for artemisinin compounds having increased selectivity and efficacy for the treatment of proliferative cellular disorders, such as cancer, infections, and other hyperproliferative conditions dependent on iron for growth and virulence. The present invention seeks to fulfill these needs and provides further related advantages.

SUMMARY OF THE INVENTION

In one aspect, the present invention provides a compound having an artemisinin-related endoperoxide moiety covalently coupled to a hydrazone moiety through a linker.

In one embodiment, the compound of the present invention has the formula (I):

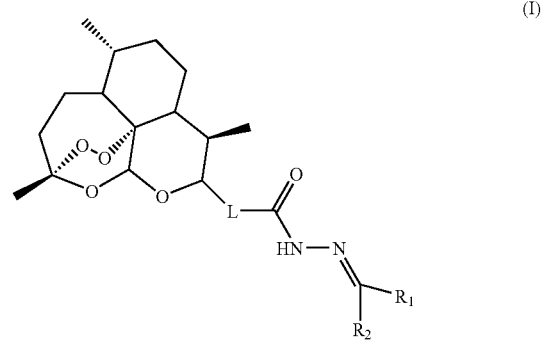

wherein L is —R—, or —O—R—, and R is selected from the group consisting of:
(a) substituted or unsubstituted arylene;
(b) substituted or unsubstituted heteroarylene;
(c) substituted or unsubstituted alkylene;
(d) substituted or unsubstituted alkenylene; and
(e) substituted or unsubstituted alkynylene;

$R_1$ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and $R_2$ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

Representative groups for R include

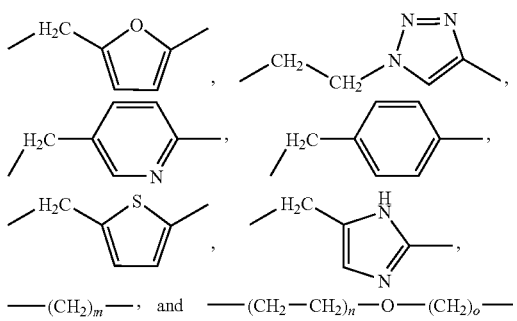

——(CH$_2$)$_m$——, and ——(CH$_2$—CH$_2$)$_n$—O—(CH$_2$)$_o$——, wherein m, n, and o are independently integers from 1 to 10.

Representative groups for R$_2$ include phenyl, 2-hydroxy phenyl, 2-methyl-3-hydroxymethyl-5-hydroxy-4-pyridyl, 2-hydroxy-1-naphthyl, 2-hydroxy-pyridyl, 2-hydroxy-furanyl, 2-hydroxy-thiofurany, and 4-hydroxyl-imidazolyl.

In one embodiment, the compound of the present invention has the formula (II):

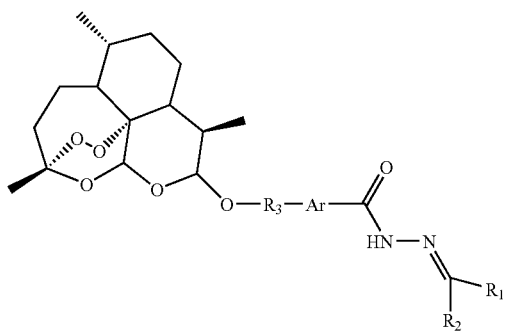

(II)

wherein R$_1$ is selected from the group consisting of:
(a) hydrogen;
(b) substituted or unsubstituted alkyl;
(c) substituted or unsubstituted alkenyl;
(d) substituted or unsubstituted alkynyl;
(e) substituted or unsubstituted aryl; and
(f) substituted or unsubstituted heteroaryl;
R$_2$ is selected from the group consisting of:
(a) substituted or unsubstituted alkyl;
(b) substituted or unsubstituted alkenyl;
(c) substituted or unsubstituted alkynyl;
(d) substituted or unsubstituted aryl; and
(e) substituted or unsubstituted heteroaryl;
R$_3$ is selected from a group consisting of:
(a) substituted or unsubstituted alkylene;
(b) substituted or unsubstituted alkenylene; and
(c) substituted or unsubstituted alkynylene; and
Ar is selected from the group consisting of:
(a) substituted or unsubstituted arylene; and
(b) substituted or unsubstituted heteroarylene.

Representative groups for R$_2$ include phenyl, 2-hydroxy phenyl, and 2-methyl-3-hydroxymethyl-5-hydroxy-4-pyridyl.

R$_3$ may be any substituted or unsubstituted alkylene such as methylene or ethylene.

Representative groups for Ar include

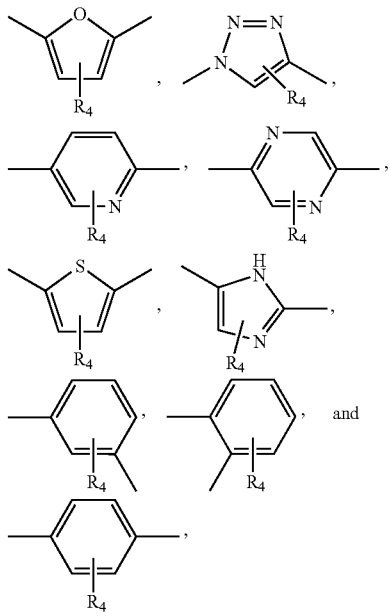

wherein R$_4$ at each position is independently selected from a group consisting of
(a) hydrogen;
(b) substituted or unsubstituted alkyl;
(c) substituted or unsubstituted alkenyl;
(d) substituted or unsubstituted alkynyl;
(e) substituted or unsubstituted aryl;
(f) hydroxy;
(g) alkoxy;
(h) dialkylamino;
(i) thio;
(j) alkylthio;
(k) carboxyl;
(l) carboxyamide;
(m) carboxyester;
(n) nitrile;
(o) halogen; and
(p) nitro.

In one embodiment, the compound of the present invention has the formula (III):

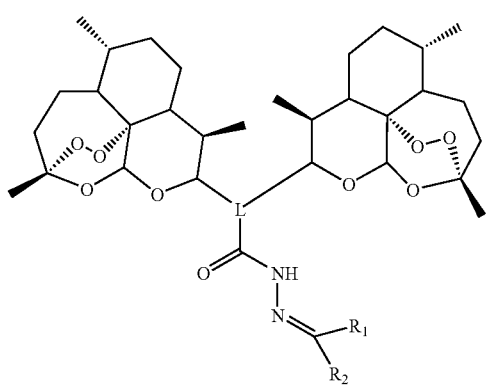

(III)

wherein L is a linker comprising one or more groups selected from the group consisting of:
(a) substituted or unsubstituted arylene;
(b) substituted or unsubstituted heteroarylene;
(c) substituted or unsubstituted alkylene;
(d) substituted or unsubstituted alkenylene; and (e) substituted or unsubstituted alkynylene;
R₁ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and
R₂ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

In another aspect, the present invention provides a composition for treating a cancer. The composition comprises a compound of the present invention (e.g., a compound having formula (I), (II), or (III)) and a pharmaceutically acceptable carrier.

In another aspect, the present invention provides a method for treating a cancer. The method includes the step of administering to a subject in need of such treatment an effective amount of a compound of the present invention (e.g., a compound having formula (I), (II), or (III)).

In one embodiment, the cancer to be treated is a cancer having an elevated transferrin receptor level. In one embodiment, the cancer is a cancer having an elevated intracellular free iron level.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

In one aspect, the invention provides a compound, comprising an artemisinin-related endoperoxide moiety covalently coupled to a hydrazone moiety through a linker.

As used herein, the term "artemisinin-related endoperoxide" refers to a compound having an endoperoxide bridge, which reacts with an iron atom to form free radicals, causing apoptosis. It would be readily apparent to a person of ordinary skill in the art that the term "artemisinin-related endoperoxide compounds" encompasses both 1,2,4-trioxane 1,2,4,5-tetraoxane derivatives. Endoperoxide compounds may also form free radicals in the presence of other types of metal ions, such as copper and manganese.

Figure 1:
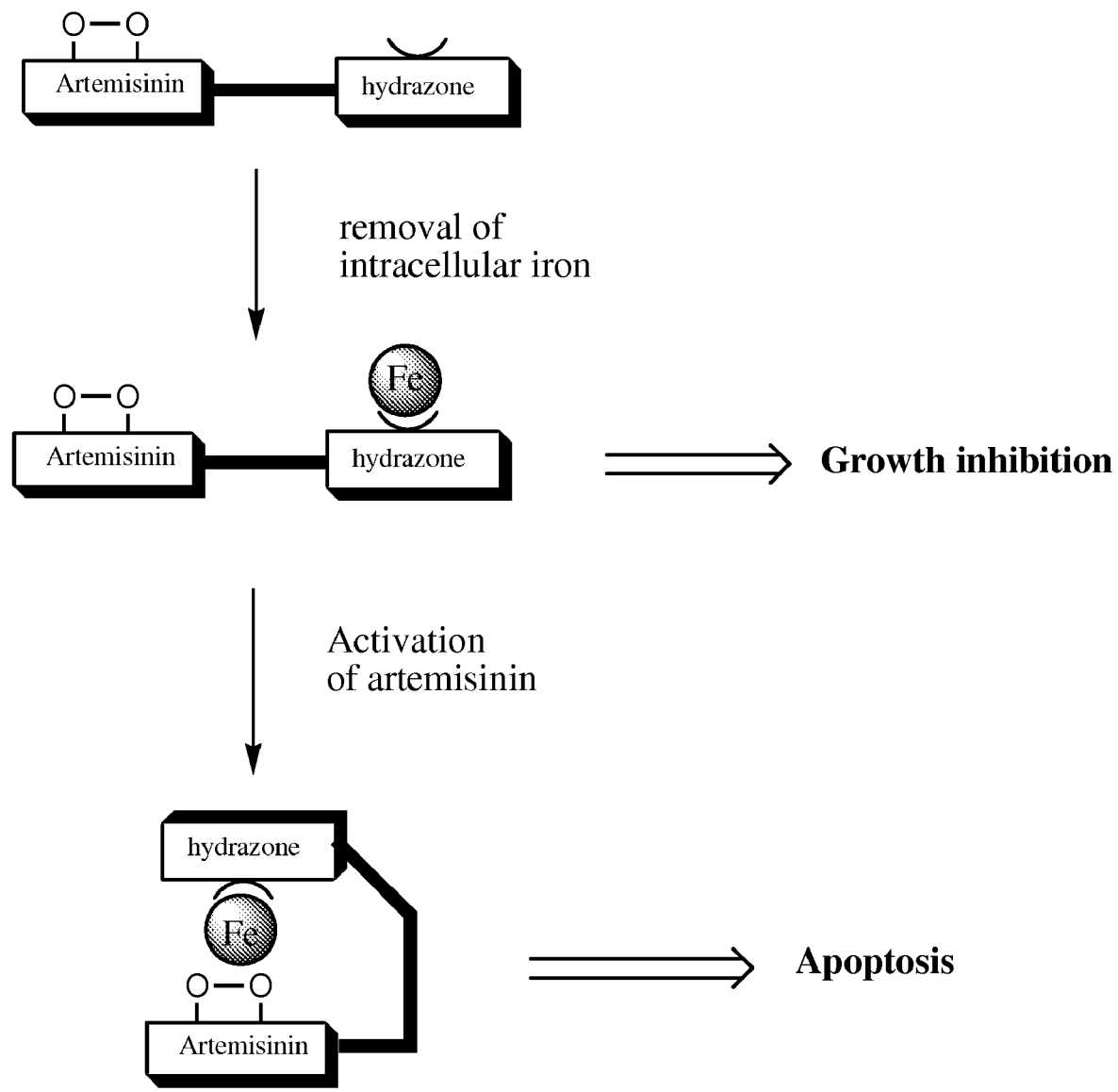
FIG. 1 schematically illustrates the mechanism of action of a compound having an artemisinin moiety covalently coupled to a hydrazone moiety through a linker.

The invention combines the cytotoxic artemisinin-related endoperoxides with the iron-chelating hydrazones to improve the selectivity and cytotoxicity of the two agents towards proliferative cellular disorders, such as cancer. Not wanting to be limited by theory, the compounds in this invention are expected to exert anti-proliferative activities by two separate and synergistic mechanisms as shown in FIG. 1: (1) the hydrazone moiety of the compound binds intracellular iron resulting in cellular growth inhibition, and brings the iron-hydrazone complex in proximity to the artemisinin moiety; and (2) the iron-hydrazone complex activates the artemisinin moiety in the same molecule to generate toxic radical species inducing cell death. For the second mechanism to be effective, the chelator should be a partial chelator, i.e., that it does not occupy all the coordination sites of the iron atom. Also, the linker between the chelator and artemisinin should be flexible and long enough to bring the partially chelated iron to the endoperoxide bridge.

The artemisinin-related endoperoxide may be derived from an artemisinin analog including artemisinin, dihydroartemisinin, artesunate, artemether, arteether, artelinic acid, artemisinin trioxane dimers, dihydroartemisinin propyl carbonate, arteflene (Ro. 42-161 1) and its analogs (Biirgen, et al. (1994) *Sixth Int. Cong. Infect. Dis. Abst.* 427, p. 152, Prague), 1,2,4-trioxanes (Peters, et al. (1993) *Ann. Trop. Med. Parasit.* 87(1):9-16), and 1,2,4,5-tetraoxanes (Vennerstrom, et al. (1992) *J. Med. Chem.* 35(16):3023-3027). Other suitable structural analogs of artemisinin useful in the invention are described in, for example, U.S. Pat. Nos. 5,216,175 and 5,180,840; Cumming, et al. (1998) *J. Med. Chem.* 41(6):952-64; and PCT patent applications WO 97101548, WO 99133461, and WO 00142046.

The source of artemisinin-related endoperoxides may be natural (e.g., isolated from plants), synthetic, semi-synthetic or recombinant. For example, the free radical-generating agents may be produced by expressing the enzymes for the relevant synthetic pathways in a microbial host, see, for example, *E. coli* or *S. cerevisiae* (Martin, et al. (2003) *Nature Biotechnol.* 21:796-802; Ro, et al. (2006) *Nature* 13; 440 (7086):940-3). Representative endoperoxide include 1,2,4-trioxanes (Peters, et al., (1993) *Ann. Trop. Med. Parasit.* 87(1):9-16) and 1,2,4,5-tetraoxanes (Vennerstrom, et al. (1992) *J. Med. Chem.* 35(16):3023-3027), although it will be apparent that other endoperoxides will be useful for this purpose.

In one embodiment, the compounds of the invention have the formula (I):

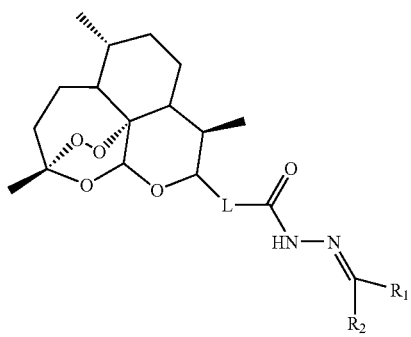

(I)

wherein L is —R—, or —O—R—, and R is selected from the group consisting of:
(a) substituted or unsubstituted arylene;
(b) substituted or unsubstituted heteroarylene;
(c) substituted or unsubstituted alkylene;
(d) substituted or unsubstituted alkenylene; and
(e) substituted or unsubstituted alkynylene;

$R_1$ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and $R_2$ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

"Alkyl" refers to alkyl groups that do not contain heteroatoms. The phrase includes primary alkyl groups, secondary alkyl groups, and tertiary alkyl groups. Therefore, the phrase includes straight chain alkyl groups such as methyl, ethyl, propyl, butyl, pentyl, hexyl, heptyl, octyl, nonyl, decyl, undecyl, dodecyl and the like, and branched chain isomers of straight chain alkyl groups. In addition, the phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Preferred alkyl groups include straight and branched chain alkyl groups and cyclic alkyl groups having 1 to 12 carbon atoms. "Alkylene" refers to the same residues as noted herein for "alkyl," but having two points of attachment, (i.e., being divalent).

"Alkenyl" refers to straight chain, branched, or cyclic radicals having one or more carbon-carbon double bonds and from 2 to about 20 carbon atoms. Preferred alkenyl groups include straight chain and branched alkenyl groups and cyclic alkenyl groups having 2 to 12 carbon atoms. "Alkenylene" refers to the same residues noted herein for "alkenyl," but having two points of attachment (i.e. divalent).

"Alkynyl" refers to straight chain, branched, or cyclic radicals having one or more carbon-carbon triple bonds and from 2 to about 20 carbon atoms. Preferred alkynyl groups include straight chain and branched alkynyl groups having 2 to 12 carbon atoms. "Alkynylene" refers to the same residues noted herein for "alkynyl," but having two points of attachment (i.e. divalent).

"Aryl" refers to monocyclic and polycyclic aromatic groups having from 3 to 14 backbone carbon and all ring atoms in the aromatic ring are carbon.

"Heteroaryl" refers herein to monocyclic and polycyclic aromatic groups having from 1 to 4 heteroatoms as ring atoms in an aromatic ring with the remainder of the ring atoms being carbon atoms.

"Substituted" refers to a group as defined above in which one or more bonds to a carbon(s) or hydrogen(s) are replaced by a bond to non-hydrogen and non-carbon atoms such as, but not limited to, a halogen atom, such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted groups also include groups in which one or more bonds to a carbon(s) or hydrogen(s) atom is replaced by a higher-order bond, such as a double- or triple-bond, to a heteroatom such as oxygen in oxo, carbonyl, carboxyl, and ester groups; nitrogen in groups such as imines, oximes, hydrazones, and nitriles. Substituted groups further include groups in which one or more bonds to a carbon(s) or hydrogen(s) atoms is replaced by a bond to an aryl, heteroaryl, heterocyclyl, or cycloalkyl group.

In one embodiment, the linker L is —O—R— and R is a substituted or unsubstituted alkylarylene. In one embodiment, the linker L is —O—R— and R is a substituted or unsubstituted alkylheteroarylene. "Alkylarylene" refers to a divalent group having a substituted or unsubstituted alkyl group covalent attached to a substituted or unsubstituted aryl group with one point of attachment on alkyl carbon and another point of attachment on an aromatic carbon. Similarly, "alkylheteroarylene" refers to a divalent group having a substituted or unsubstituted alkyl group covalent attached to a substituted or unsubstituted heteroaryl group with one point of attachment on alkyl carbon and another point of attachment on an aromatic atom.

Representative linkers (L) include

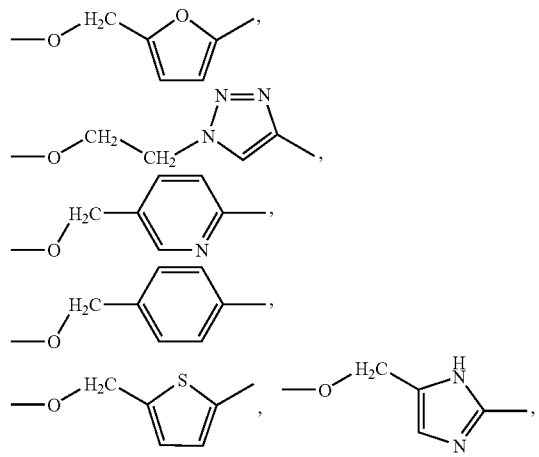

-continued

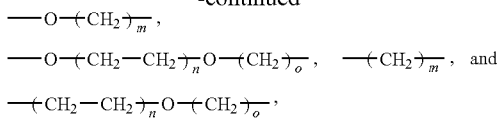

wherein m, n, and o are independently selected from an integer from 1 to 10.

Representative $R_1$ groups include phenyl, 2-hydroxy phenyl, 2-methyl-3-hydroxymethyl-5-hydroxy-4-pyridyl, 2-hydroxy-1-naphthyl, 2-hydroxy-pyridyl, 2-hydroxy-furanyl, 2-hydroxy-thiofuranyl, and 4-hydroxyl-imidazolyl.

In one embodiment, the compounds of the invention have the formula (II):

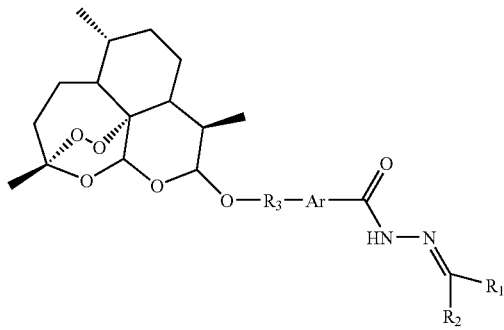

(II)

wherein $R_1$ is selected from the group consisting of:
(a) hydrogen;
(b) substituted or unsubstituted alkyl;
(c) substituted or unsubstituted alkenyl;
(d) substituted or unsubstituted alkynyl;
(e) substituted or unsubstituted aryl; and
(f) substituted or unsubstituted heteroaryl;
$R_2$ is selected from the group consisting of:
(a) substituted or unsubstituted alkyl;
(b) substituted or unsubstituted alkenyl;
(c) substituted or unsubstituted alkynyl;
(d) substituted or unsubstituted aryl; and
(e) substituted or unsubstituted heteroaryl;
$R_3$ is selected from a group consisting of:
(a) substituted or unsubstituted alkylene;
(b) substituted or unsubstituted alkenylene; and
(c) substituted or unsubstituted alkynylene; and
Ar is selected from the group consisting of:
(a) substituted or unsubstituted arylene; and
(b) substituted or unsubstituted heteroarylene.

Representative $R_2$ groups include phenyl, 2-hydroxy phenyl, and 2-methyl-3-hydroxymethyl-5-hydroxy-4-pyridyl.

Representative $R_3$ groups include lower alkylene, such as methylene or ethylene.

The group Ar can be any divalent substituted or unsubstituted monocyclic and polycyclic aromatic groups having from 3 to 14 backbone carbon or hetero atoms. "Arylene" refers to divalent aryl groups in which all ring atoms in the aromatic ring are carbon. "Heteroarylene" refers to divalent aryl groups having from 1 to 4 heteroatoms as ring atoms in an aromatic ring with the remainder of the ring atoms being carbon atoms. "Polycyclic aromatic group" refers herein to fused and non-fused cyclic structures in which at least one cyclic structure is aromatic, such as naphthyl. The monocyclic and polycyclic aromatic groups can be substituted at various positions as will be apparent to those having skill in the organic and medicinal chemistry arts in conjunction with the disclosure herein. Representative groups for Ar include:

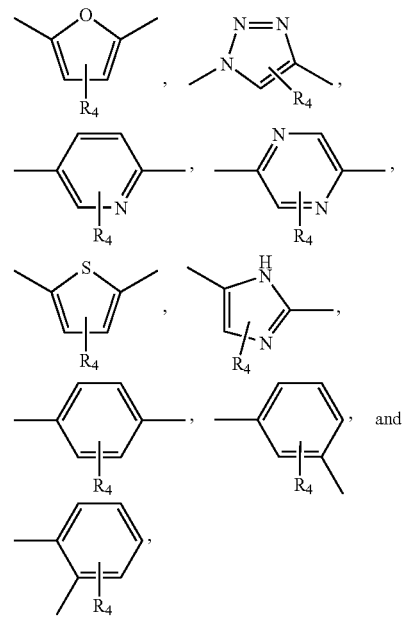

wherein $R_4$ at each position is independently selected from a group consisting of:
(a) hydrogen;
(b) substituted or unsubstituted alkyl;
(c) substituted or unsubstituted alkenyl;
(d) substituted or unsubstituted alkynyl;
(e) substituted or unsubstituted aryl;
(f) hydroxy;
(g) alkoxy;
(h) dialkylamino;
(i) thio;
(j) alkylthio;
(k) carboxyl;
(l) carboxyamide;
(m) carboxyester;
(n) nitrile;
(o) halogen; and
(p) nitro.

The artemisinin moiety in the compounds of the present invention can be derived from any suitable artemisinin derivative, such as dihydroartemisinin or its ester. The hydrazone moiety can be formed through the coupling between a carbohydrazide with either an aldehyde or a ketone. Representative compounds of the invention include:

N'-(2-hydroxybenzylidene)-5-(dihydroxyartemisinin-methyl)-furan-2-carbohydrazide (ART-Furan-Sal);
N'-(2-hydroxybenzylidene)-1-(dihydroxyartemisinin-ethyl)-1H-1,2,3-triazole-4-carbohydrazide (ART-Triazole-Sal);
N'-(2-hydroxybenzylidene)-5-(dihydroxyartemisinin-methyl)-2-pyridine carbohydrazide (ART-Pyr-Sal);
N'-(2-hydroxybenzylidene)-4-(dihydroxyartemisinin-methyl)-phenyl carbohydrazide (ART-Phe-Sal);
N'-(benzylidene)-4-(dihydroxyartemisinin-methyl)-phenyl carbohydrazide (ART-Phe-Bz);

N'-(5-hydroxy-3-hydroxymethyl-2-methyl-4-pyridylidene)-4-(dihydroxyartemisinin-methyl)-phenyl carbohydrazide (ART-Phe-Pyridoxal);

N'-(2-hydroxybenzylidene)-(2E)-4-(dihydroartemisin-methyl)-2-butenoic hydrazide (ART-Butenoic-Sal); and N'-(2-hydroxybenzylidene)-4-(dihydroartemisin-methyl)-2-butynoic hydrazide (ART-Butynoic-Sal).

As shown in FIGS. 2-9, the artemisinin moiety of the above representative compounds is derived from an artemisinin moiety precursor such as dihydroxyartemisinin (DHA) or its ester, acetyl-dihyroxyartemisinin. A bifunctional precursor for the linker moiety is coupled to the aremisinin moiety precursor followed by the reaction with anhydrous hydrazine to afford a carbohydrazide, which is then coupled with an aldehyde or ketone to afford a hydrazone, the compound of the present invention.

Figure 5:
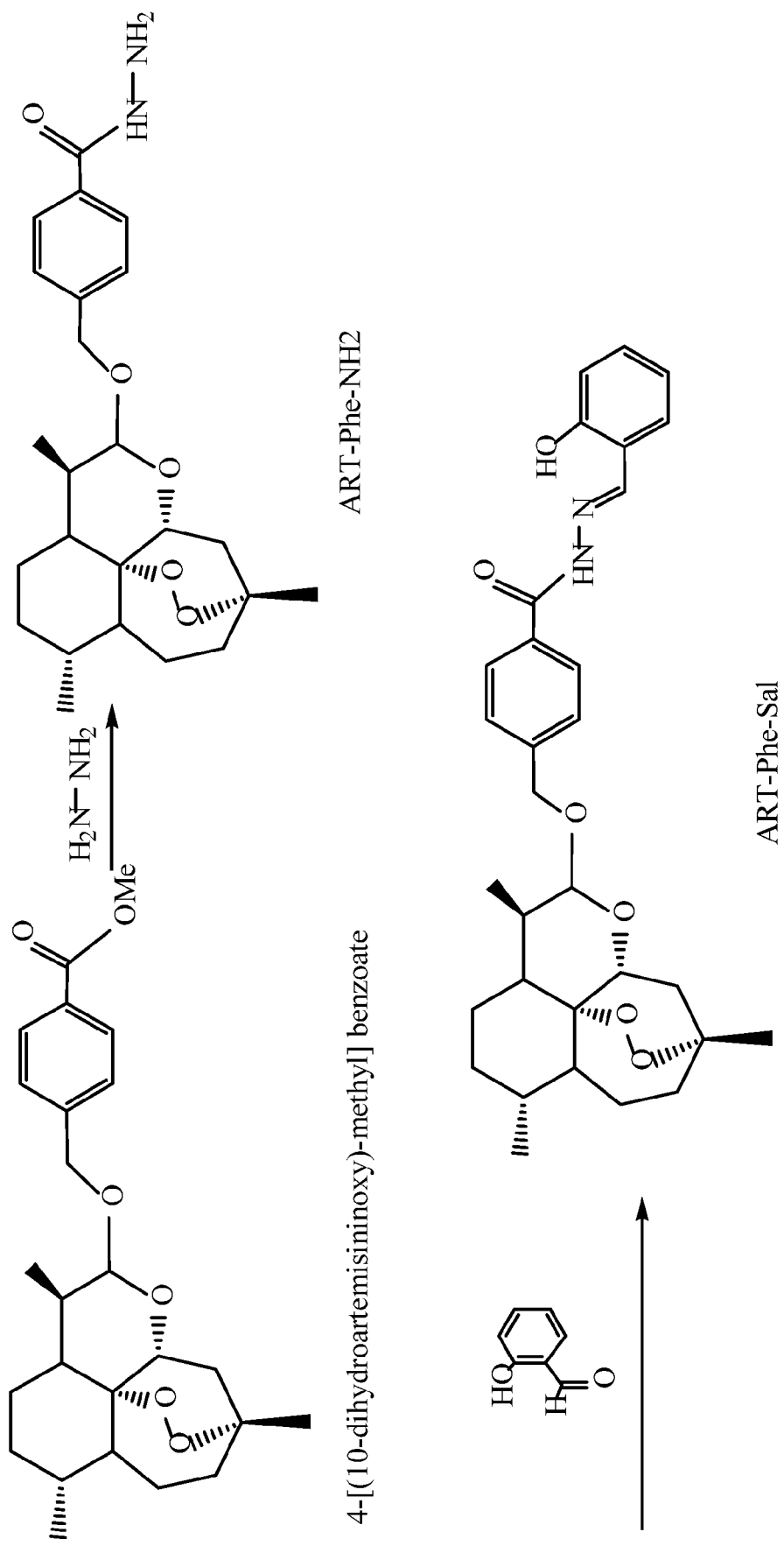
FIG. 5 shows the synthesis of a representative compound N'-(2-hydroxybenzylidene)-4-(dihydroxyartemisinin-methyl)-phenyl carbohydrazide (ART-Phe-Sal)
Figure 6:
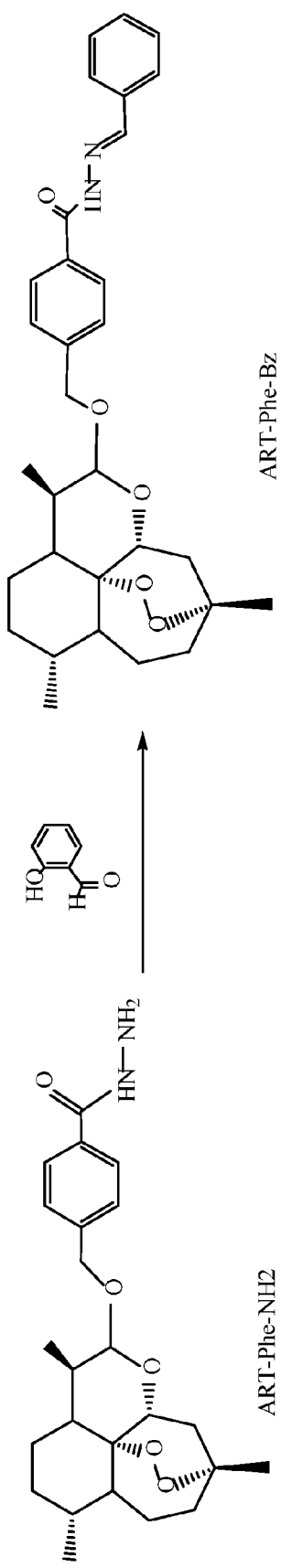
FIG. 6 shows the synthesis of a representative compound N'-(benzylidene)-4-(dihydroxyartemisinin-methyl)-phenyl carbohydrazide (ART-Phe-Bz)
Figure 7:
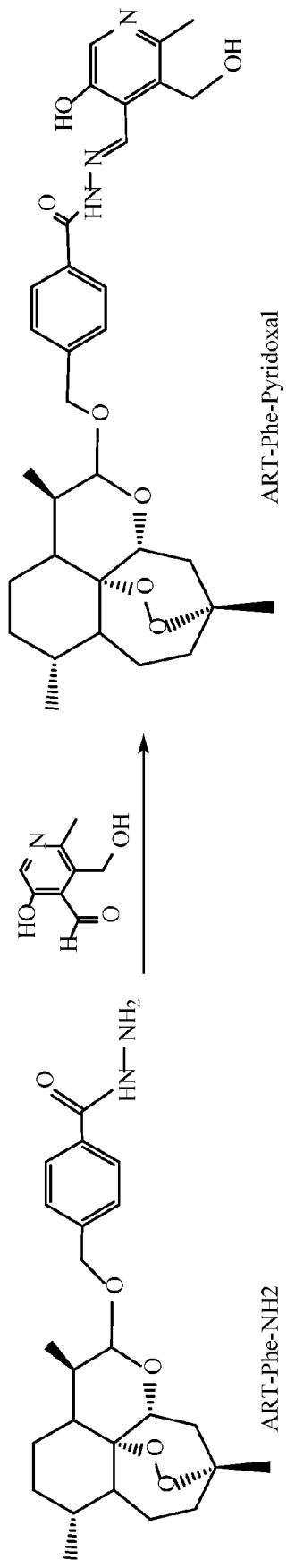
FIG. 7 shows the synthesis of a representative compound N'-(5-hydroxy-3-hydroxymethyl-2-methyl-4-pyridylidene)-4-(dihydroxyartemisinin-methyl)-phenyl carbohydrazide (ART-Phe-Pyridoxal)

In one embodiment, the precursor for the linker moiety comprises substituted or unsubstituted aryl, or substituted or unsubstituted heteroaryl. Representative precursors for the linker moiety having an aromatic ring include methyl 5-(hydroxymethyl)-furan-2-carboxylate (FIG. 2), methyl 1-(2-hydroxymethyl)-1H-1,2,3-triazole-4-carboxylate (FIG. 3), 5-hydroxymethyl-2-ethyl pyridine carboxylate (EHMP) (FIG. 4), and 4-methyoxy benzoate (FIGS. 5-7).

Figure 8:
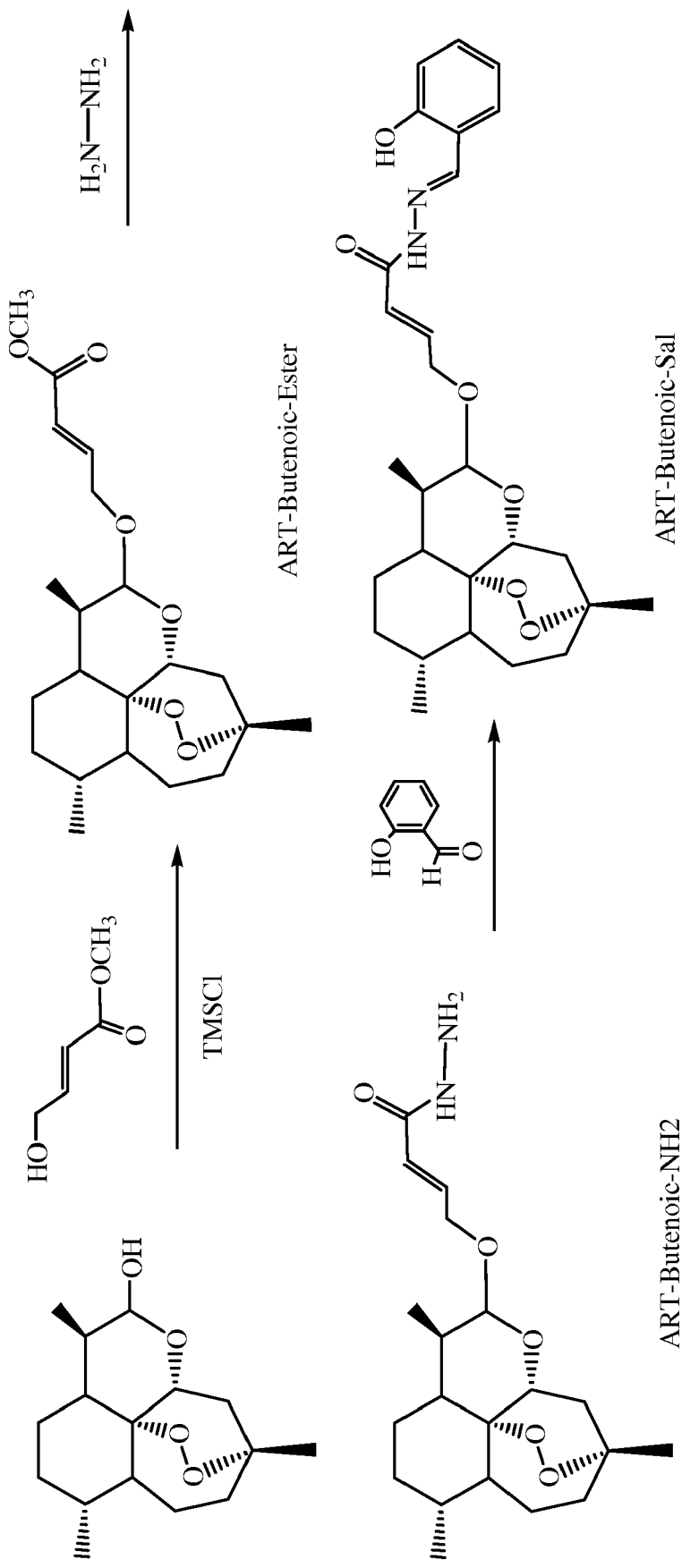
FIG. 8 shows the synthesis of a representative compound N'-(2-hydroxybenzylidene)-(2E)-methyl-4-dihydroartemisin-2-butenoic hydrazide (ART-Butenoic-Sal)

In one embodiment, the precursor for the linker moiety comprises substituted or unsubstituted alkenyl. Representative precursors for the linker moiety having one or more carbon-carbon double bond include (2E)-methyl-4-hydroxy-2-butenoate, as shown in FIG. 8.

Figure 9:
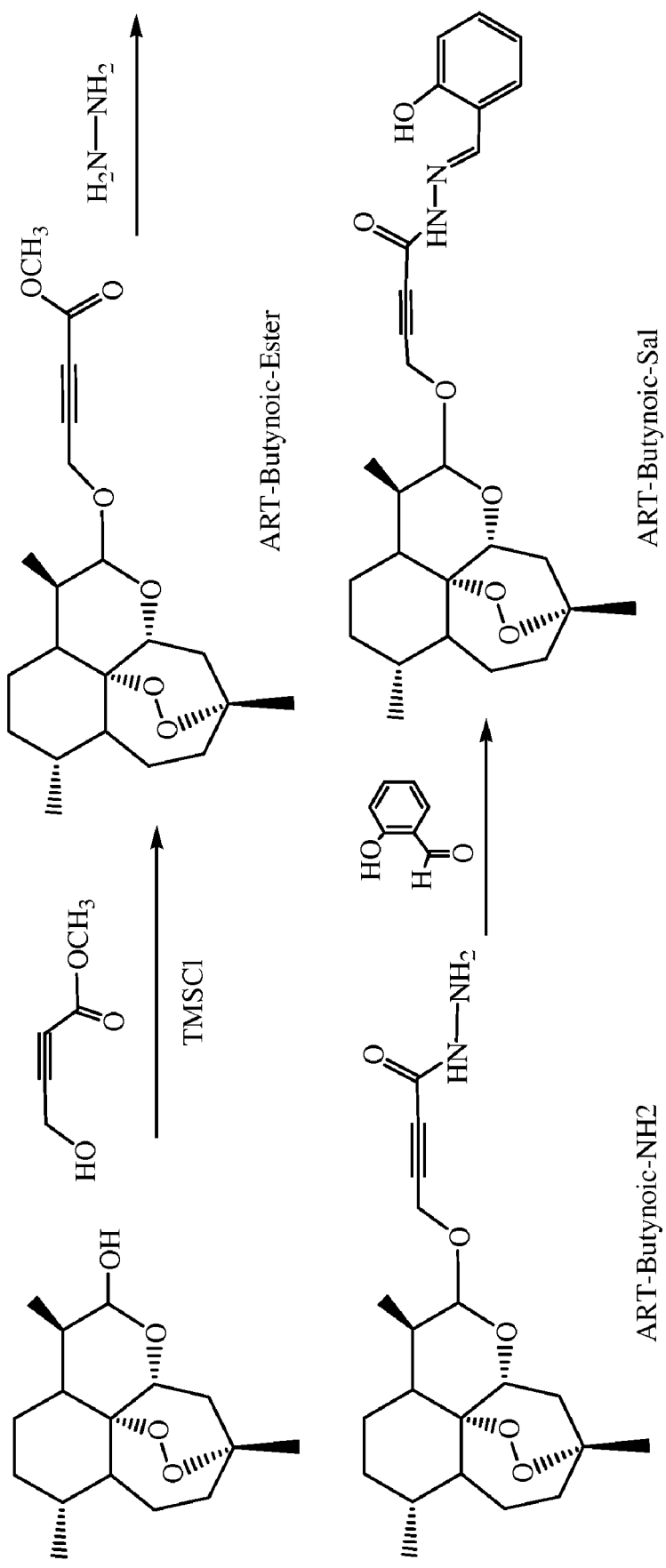
FIG. 9 shows the synthesis of a representative compound N'-(2-hydroxybenzylidene)-methyl-4-dihydroartemisin-2-butynoic hydrazide (ART-Butynoic-Sal)

In one embodiment, the precursor for the linker moiety comprises substituted or unsubstituted alkynyl. Representative precursors for the linker moiety having one or more carbon-carbon triple bond include methyl 4-hydroxy-2-butynoate, as shown in FIG. 9.

In one embodiment, compounds of the invention have the formula (III):

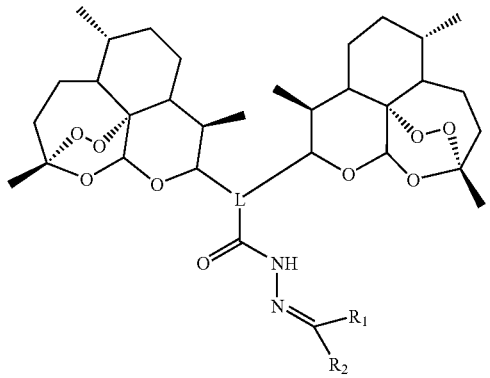

(III)

wherein L is a linker comprising one or more groups selected from the group consisting of:
(a) substituted or unsubstituted arylene;
(b) substituted or unsubstituted heteroarylene;
(c) substituted or unsubstituted alkylene;
(d) substituted or unsubstituted alkenylene; and
(e) substituted or unsubstituted alkynylene;

$R_1$ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and $R_2$ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

Linker L includes at least one trivalent atom or group. In one embodiment, L is —$CH_2$—CH—$CH_2$—.

Figure 10:
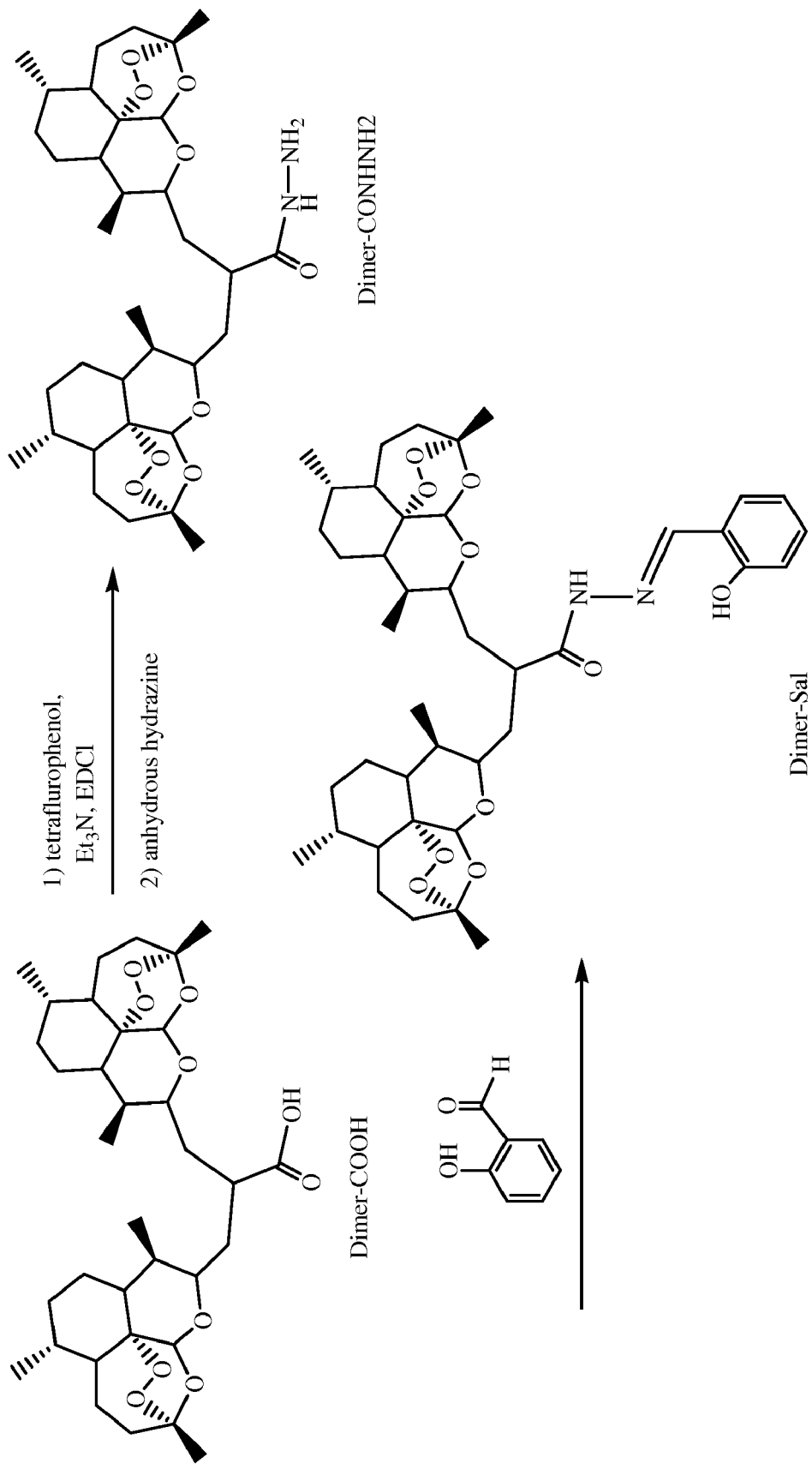
FIG. 10 shows the synthesis of a representative compound 4-(dihydroxyartemisinin-methyl)-phenyl carbohydrazide (Dimer-Sal)

As shown in FIG. 10, a representative compound, 4-(dihydroxyartemisinin-methyl)-phenyl carbohydrazide (Dimer-Sal), can be synthesized from dimer-COOH, following by the reaction with anhydrous hydrazine, which was then coupled to an aldehyde to afford a hydrazone compound, N'-(2-hydroxybenzylidene)-2,2'-(bis-10-deoxyartemisinin-10β-methyl)-acetyl carbohydrazide (Dimer-Sal).

In another aspect, the invention provides compositions for treating cancer. The composition of the invention includes one or more compounds of the invention (e.g., a compound having formula (I), (II), or (III)). The composition includes a compound having an artemisinin-related endoperoxide moiety covalently coupled a hydrazone moiety through a linker.

In one embodiment, the compounds of the invention may be formulated into a composition that additionally comprises suitable pharmaceutically acceptable carriers, including excipients and other compounds that facilitate administration of the covalent conjugate to a mammalian subject. Further details on techniques for formulation and administration may be found in the latest edition of "Remington's Pharmaceutical Sciences" (Mack Publishing Co, Easton, Pa.).

Compositions for oral administration may be formulated using pharmaceutically acceptable carriers well known in the art, in dosages suitable for oral administration. Such carriers enable the compositions containing compounds of the invention to be formulated as Tablets, pills, dragees, capsules, liquids, gels, syrups, slurries, suspensions, etc., suitable for ingestion by a subject. Compositions for oral use may be formulated, for example, in combination with a solid excipient, optionally grinding the resulting mixture, and processing the mixture of granules, after adding suitable additional compounds, if desired, to obtain Tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins, such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compositions for oral administration may be formulated, for example, as push-fit capsules made of gelatin, as well as soft, sealed capsules made of gelatin and a coating such as glycerol or sorbitol. Push-fit capsules may contain the compounds of the invention mixed with filler or binders such as lactose or starches, lubricants such as talc or magnesium stearate, and, optionally, stabilizers. In soft capsules, the compounds of the invention may be dissolved or suspended in suitable liquids, such as fatty oils, liquid paraffin, or liquid polyethylene glycol with or without stabilizers.

Compositions for parenteral administration include aqueous solutions of one or more compounds of the invention. For injection, the compounds may be formulated in aqueous solutions, such as in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the compounds to allow for the preparation of highly concentrated solutions.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences-Dekker); Harrys Cosmeticology (Leonard Hill Books).

For rectal administration, the compositions may be administered in the form of suppositories or retention enemas. Such compositions may be prepared by mixing the compounds of the invention with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

Compositions containing the compounds of the invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the compounds may be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain the compounds of the invention and an acceptable carrier have been prepared, they can be placed in an appropriate container and labeled for use.

In another aspect, the invention provides methods for treating cancer, particularly cancers associated with elevated transferrin receptor expression or an increase in intracellular free iron.

Transferrin is an iron carrying protein. Transferrin carries iron ion across the cell membrane and iron is released from transferrin intracellularly. Cancer cells, in general, have a high cell surface concentration of transferrin receptors, which leads to higher intake of iron inside the cancer cell. A variety of cancers are known to be associated with elevated transferrin receptor expression. Table 1 provides a summary of literature references, grouped by cancer type.

TABLE 1

| Cancers with Elevated Transferrin Receptor Expression | |
| --- | --- |
| Liver Cancer and Hepatitis C | Sciot, R., et al., Histopathology 12(1): 53-63, January 1988. |
| | Lee, A. W., et al., Hepatology 38(4): 967-77, October 2003. |
| | Pascale, R. M., et al., Hepatology 27(2): 452-61, February 1998. |
| | Lin, J., Zhonghua Yi Xue Za Zhi 72(2): 86-7, 128, February 1992. |
| | Sciot, R. et al., Histopathology 16(1): 59-62., January 1990. |
| | Bolewska, B. et al., Pol. Merkur. Lekarski. 18(107): 552-5, May, 2005. |
| | Saito, H., et al., Hepatol. Res. 31(4): 203-10, April 2005. |
| Pancreatic Cancer | Buchler, M. W., et al., Eur. J. Cancer40(9): 1418-22, June 2004. |
| Breast Cancer | Wrba, F. et al., Virchows. Arch. A. Pathol. Anat. Histopathol. 410(1): 69-73, 1986.. |
| | Hogemann-Savellano, D. et. al., Neoplasia 5(6): 495-506, November-December 2003.. |
| | Yang, D. C., et al., Anticancer. Res. 21(3B): 1777-87. May-June 2001. |
| | Yang, D. C., et al., Anticancer Res. 21(1B): 541-9, January-February 2001. |
| | Cavanaugh, P. G., et al., Breast Cancer Res. Treat. 56(3): 203-17, August 1999. |
| Lung Cancer | Anabousi, S., et al., Eur. J. Pharm. Sci. 29(5): 367-74, December 2006, Epub Jul. 22, 2006. |
| | Dowlati, A., et al., Br. J. Cancer 75(12): 1802-6, 1997. |
| | Carbognani, P. et al., Cancer 78(1): 178-9, Jul. 1, 1996. |
| | Whitney, J. F., et al., Cancer. 76(1): 20-5, Jul. 1, 1996. |
| | Kayser, K., and Ernst M, Bubenzer J., Exp. Pathol. 41(1): 37-43, 1991. |
| | Kondo, K., et al., Chest 97(6): 1367-71, June 1990. |
| | Vostrejs, M., et al., J. Clin. Invest. 82(1): 331-9, July 1988. |
| Gastric Cancer | Yuan, P. X., and L. S. Si, Zhonghua Bing Li Xue Za Zhi 21(2): 88-91, April 1992. |
| | Iinuma, H., et al., Int. J. Cancer 99(1): 130-7, May 1, 2002. |
| Colorectal Cancer | Brookes, M. J., et al., Gut 55(10): 1449-60, October 2006, Epub Apr. 26, 2006. |
| | Prutki, M., et al., Cancer Lett. 238(2): 188-96, Jul. 18, 2006, Epub Aug. 18, 2005. |
| Leukemia | Shackelford, R. E., et al., Med. Hypotheses 66(3): 509-12, 2006, Epub Dec. 2, 2005. |
| | Smilevska, T., et al., Leuk. Res. 30(2): 183-9, February 2006, Epub Jul. 28, 2005. |
| | Staber, P. B., et al., Oncogene 23(4): 894-904, Jan. 29, 2004. |
| | Huang, G., et al., Hua Xi Yi Ke Da Xue Xue Bao 28(1): 55-7, March 1997. |
| | Petrini, M., et al.., Cancer Res. 49(24 Pt 1): 6989-96, Dec. 15, 1989 |
| | Barnett, D., et al., Clin. Lab. Haematol. 9(4): 361-70, 1987. |
| Cervical Cancer | Disbrow, G. L., et al., Cancer Res. I(23): 10854-61, Dec. 1, 2005. |
| | Farley, J., et al., Anal. Quant. Cytol. Histol. 20(4): 238-49, August 1998. |

TABLE 1-continued

Cancers with Elevated Transferrin Receptor Expression

| | |
|---|---|
| Ovarian Cancer | Hereiz, H. A., and F. A. Bayoumi. J. Egypt Public Health Assoc. 67(5-6): 697-707, 1992.<br>Lloyd, J. M., et al., J. Clin. Pathol. 37(2): 131-5., February 1984. |
| Brain Cancer | Ucar, T., and I. Gurer, Br. J. Neurosurg. 17(6): 525-9, December 2003.<br>Wen, D. Y., et al., Neurosurgery 36(6): 1158-63; discussion 1163-4, June 1995.<br>Martell, L. A., et al., Cancer Res. 53(6): 1348-53, Mar. 15, 1993.<br>Prior, R., et al., Virchows. Arch. A. Pathol. Anat. Histopathol. 416(6): 491-6, 1990.<br>Hall, W. A., et al.., J. Neurosurg. 76(5): 838-44, May 1992. |
| Non-Hodgkin's Lymphoma | Nejmeddine, F., et al., J. Nucl. Med. 40(1): 40-5, January 1999.<br>Das Gupta, A., and V. I. Shah, Hematol. Pathol. 4(1): 37-41, 1990. |
| Head and Neck Cancer | Kearsley, J. H., et al., Br. J. Cancer 61(6): 821-7, June 1990<br>Barresi, G., and G. Tuccari, Pathol. Res. Pract. 182(3): 344-51, June 1987. |
| Pituitary Cancer | Tampanaru-Sarmesiu, A., et al., Am. J. Pathol. 152(2): 413-22, February 1998. |
| Oral Cancer | Miyamoto, T., et al., Int. J. Oral Maxillofac. Surg. 23(6 Pt 2): 430-3, December 1994.<br>Miyamoto, T., Kokubyo Gakkai Zasshi 59(1): 21-32, March 1992.<br>Tanaka, N., et al., Bull Tokyo Med. Dent. Univ. 38(3): 19-26, September 1991. |
| Bladder Cancer | Derycke, A. S., et al., J. Natl. Cancer Inst. 96(21): 1620-30, Nov. 3, 2004.<br>Limas, C., J. Pathol. 171(1): 39-47, September 1993.<br>Smith, N. W., et al., Br. J. Urol. 65(4): 339-44, April 1990.<br>Seymour, G. J., et al., Urol. Res. 15(6): 341-4, 1987. |
| Melanoma | van Muijen, G. N., et al., Int. J. Cancer 48(1): 85-91, Apr. 22, 1991.<br>Soyer, H. P., et al., J. Cutan. Pathol. 14(1): 1-5, February 1987.<br>Iwata, M., et al., J. Dermatol. 15(3): 208-11, June 1988.<br>Richardson, D. R., Biochim. Biophys. Acta 1091(3): 294-302, Feb. 19, 1991. |
| Prostate Cancer | Keer, H. N., et al., J. Urol. 143(2): 381-5, February 1990.<br>Sahoo, S. K., et al., Int. J. Cancer 112(2): 335-40, Nov. 1, 2004.<br>Rossi, M. C., and B. R. Zetter, Proc. Natl. Acad. Sci. USA 89(13): 6197-201, Jul. 1, 1997. |
| Biliary Cancer | Tuccari G et al., Histol Histopathol 1997 Jul; 12(3): 671-6. |

An ideal requirement for cancer chemotherapy is that the therapeutic agent act specifically on cancer cells, with little toxicity towards normal cells. Artemisinin has been shown to have relatively high selectivity on cancer cells, e.g., it has a therapeutic index (i.e., toxicity towards cancer cells versus normal cells) of approximately 100 on human leukemia cells. This is due to cancer cells picking up and sequestering a high concentration of iron that reacts with artemisinin and other artemisinin-related endoperoxides. Iron converts artemisinin-related endoperoxides into free radicals that induce apoptosis.

The inventors have found that the covalently coupling artemisinin-related endoperoxides to iron-chelating agents, such as hydrazones, increases the selectivity and cytotoxicity of artemisinin-related endoperoxides towards cancer cells. Accordingly, the cancer that may be treated by using the compounds of the invention includes cancers with cancer cells having elevated transferrin receptor level or increased intracellular free iron, such as lung cancer, especially non-small cell lung cancer, colorectal cancer, breast cancer, cervical cancer, ovarian cancer, leukemia, renal cancer, melanoma, prostate cancer, CNS cancer, fibrosarcoma, head and neck cancer, Kaposi's sarcoma, lymphoma, liver cancer, multiple myeloma, oral cancer, pituitary cancer, biliary cancer, bladder cancer, gastric cancer, non-Hodgkin's lymphoma, and pancreatic cancer.

Figure 11:
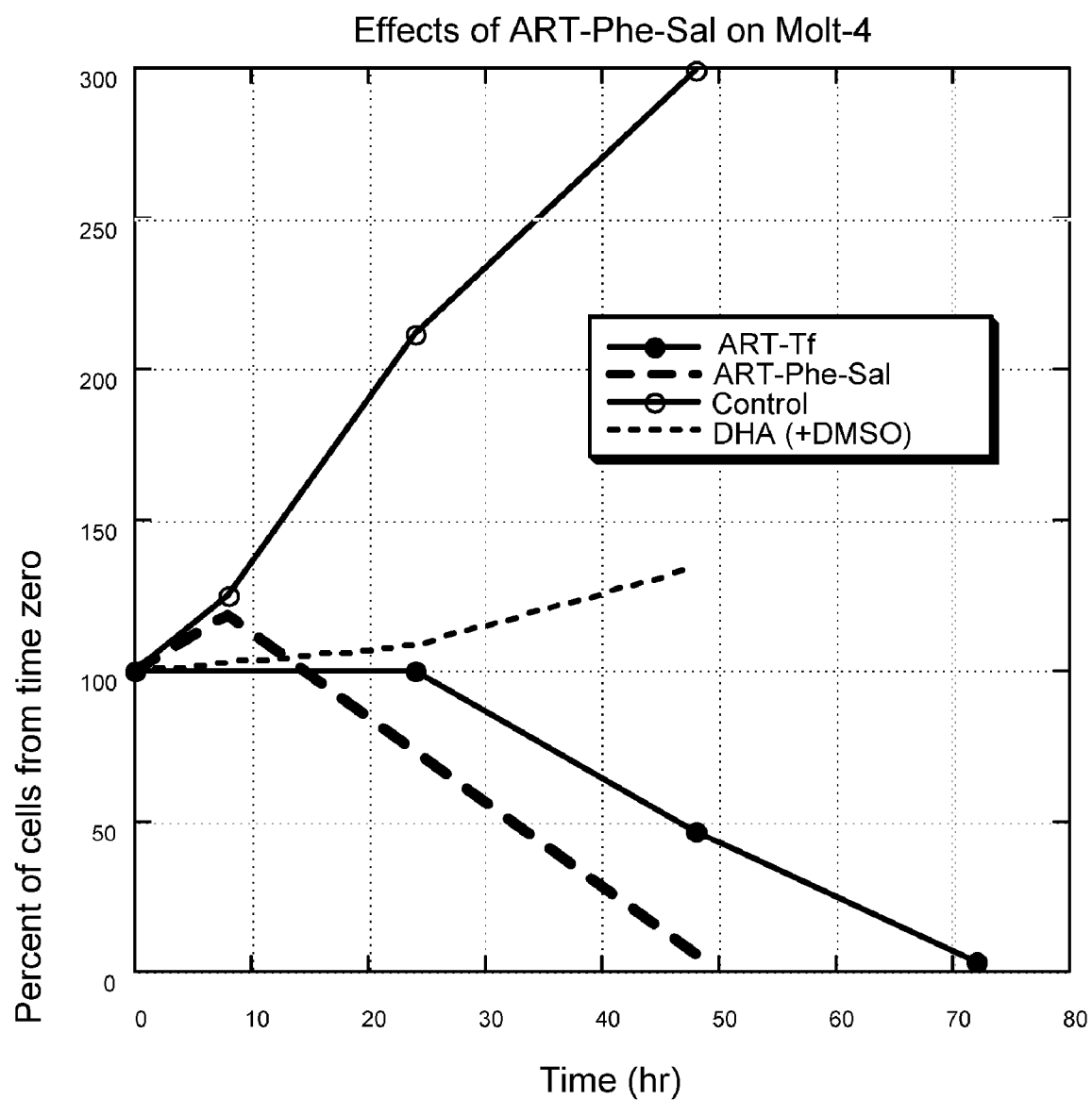
FIG. 11 compares the effect of ART-Phe-Sal, dihydroartemisinin (DHA), and artemisinin-transferrin conjugate (ART-Tf) on human Molt-4 cells.
Figure 12:
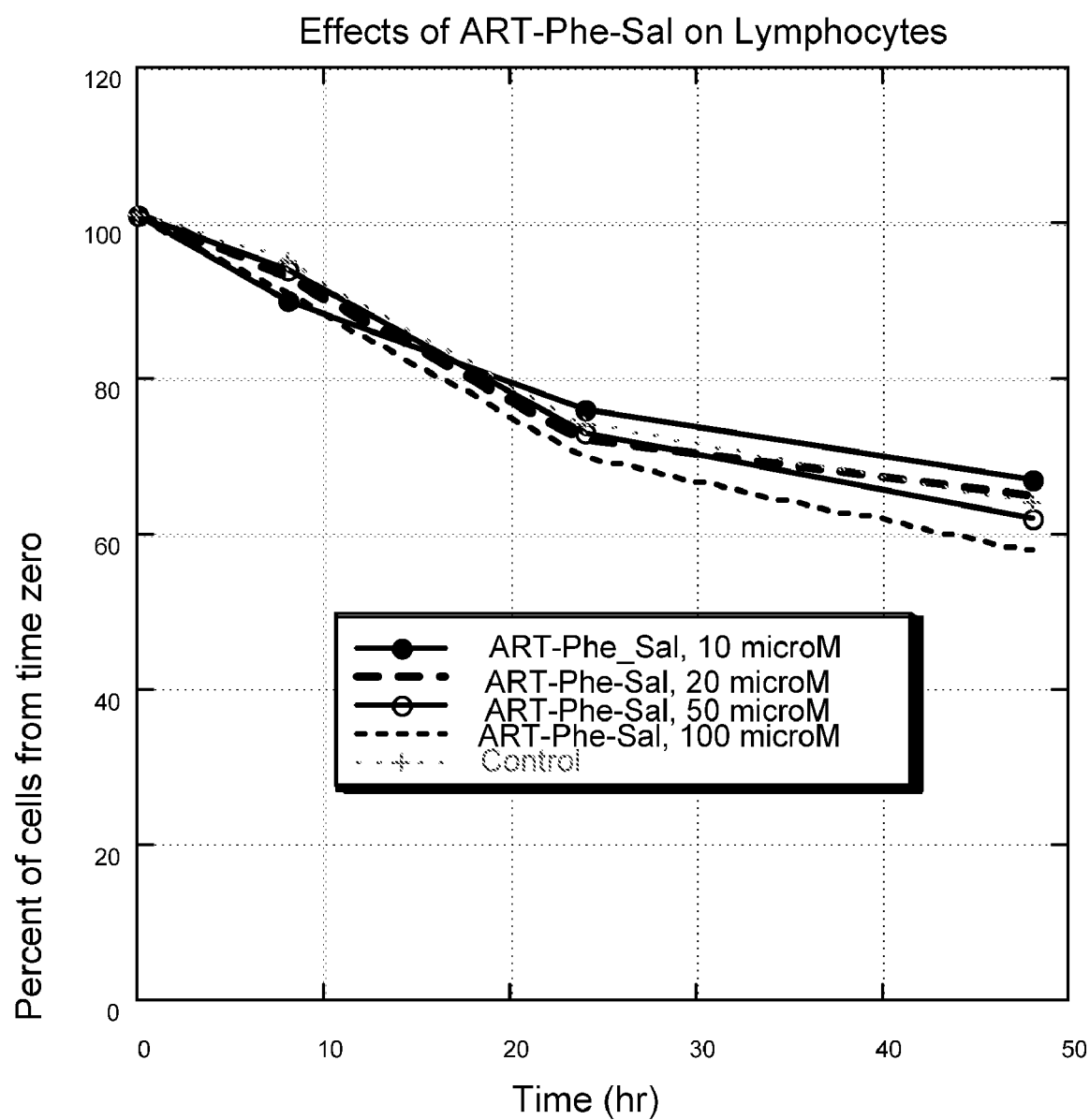
FIG. 12 shows the effect of ART-Phe-Sal on human lymphocytes.

As shown in FIGS. 11 and 12, the invention has demonstrated in vitro that a representative compound having an artemisinin moiety covalently coupled to a hydrazone moiety, ART-Phe-Sal, can effectively kill human leukemia cells without affecting normal lymphocytes. Further, FIG. 13 demonstrates that ART-Phe-Sal is active against DAOY medulloblastoma cells.

In addition, representative compounds of the invention including ART-Furan-Sal, ART-Triazole-Sal, ART-Pyr-Sal, ART-Phe-Sal, and ART-Phe-Pyridoxal have been subjected to the DTP human tumor cell line screen provided by the National Cancer Institute. The results demonstrate that the compounds of the invention have inhibitory activities against several types of cancer cells including non-small cell lung cancer, colon cancer, breast cancer, ovarian cancer, leukemia, renal cancer, melanoma, prostate cancer, and CNS cancer.

These methods are applicable to any animal subject, such as a human subject. For example, a subject in need of compositions comprising a compound of the invention may be a cancer patient. As described above, rapidly proliferating cells such as cancer cells generally need higher concentrations of iron to sustain the rapid proliferation of cells, and typically have a higher concentration of intracellular free iron compared to normal cells. Thus, the compounds of this invention could be more toxic to cancer cells than normal cells. The methods provide a mechanism for selectively delivering both an endoperoxide moiety and the iron it reacts with to rapidly proliferating cells, such as cancer cells. Accordingly, the invention provides methods for treating cancer by administering to a human or animal subject in need thereof an effective amount of a compound of invention.

Effective amounts of the compound will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Compounds that exhibit large therapeutic indices are particularly suitable in the practice of the methods of the invention. The data obtained from cell culture assays and animal studies may be used in formulating a range of dosage for use in humans or other mammals. The dosage of such conjugates lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the invention may be administered alone, or in combination with one or more additional therapeutically active agents. For example, in the treatment of cancer, the conjugates may be administered in combination with therapeutic agents including, but not limited to, androgen inhibitors, such as flutamide and luprolide; antiestrogens, such as tomoxifen; antimetabolites and cytotoxic agents, such as daunorubicin, epirubicin, fluorouracil, floxuridine, interferon alpha, methotrexate, plicamycin, mercaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idarubicin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; targeted anticancer agents and biologics, such as imatinib, gefitinib, erlotinib, bortezomib, oblimersen, trastuzumab, bevacizumab, rituximab, gemtuzumab, alemtuzumab, ibritumomab, tostumomab, cetuximab, panitumumab, and interleukins; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

The compounds of the invention may also be administered in combination with an agent that increases iron transport into cells. It has been shown for example, that insulin, insulin-like growth factor I, and epidermal growth factor cause an increase in the number of transferrin receptors at the cells surface (see, e.g., Davis et al. (1987) *J. Biol. Chem.* 261(19): 8708-11; Davis et al. (1986) *J. Biol. Chem.* 262(17):13126-34). Therefore, in some embodiments, the compounds of the invention are administered in combination with insulin, insulin-like growth factor I, or epidermal growth factor.

The compounds of the invention may also be combined with agents such as cytokines, growth factors, and other compounds that are iron-regulating molecules that enhance transferrin expression and/or intracellular iron to facilitate the treatment of cancer. Exemplary compounds include, but are not limited to, erythropoietin, interleukin-4, interleukin-10, interleukin-13, and dexrazoxane.

Administration of the compounds of the invention is accomplished by any effective route, e.g., parenterally or orally. Methods of administration include topical (for examples, skin patches), inhalational, buccal, intraarterial, subcutaneous, intramedullary, intravenous, intranasal, intrarectal, intraocular administration, and other conventional means. For example, the covalent conjugates may be injected directly into a tumor, into the vicinity of a tumor, or into a blood vessel that supplies blood to the tumor.

The compounds of the invention are useful in the manufacture of a medicament for the treatment of cancer.

Each citation noted herein is expressly incorporated herein by reference in its entirety.

The following examples are provided for the purpose of illustrating, not limiting, the invention.

EXAMPLES

The covalent conjugates of the invention are generally prepared by reacting an aldehyde with an endoperoxide moiety that carries a hydrazine (R,R'N—$NH_2$) (FIGS. 2-10). The linker between the endoperoxide moiety and the iron chelating moiety, such as a hydrazone, can be by any covalent bond means. In the sections below, the syntheses of representative compounds of the invention are described.

All parts are by weight, and temperatures are indicated in degrees centigrade (° C.), unless otherwise indicated.

Example 1

Synthesis of N'-(2-hydroxybenzylidene)-5-(dihydroxyartemisinin-methyl)-furan-2-carbohydrazide (ART-Furan-Sal)

Figure 2:
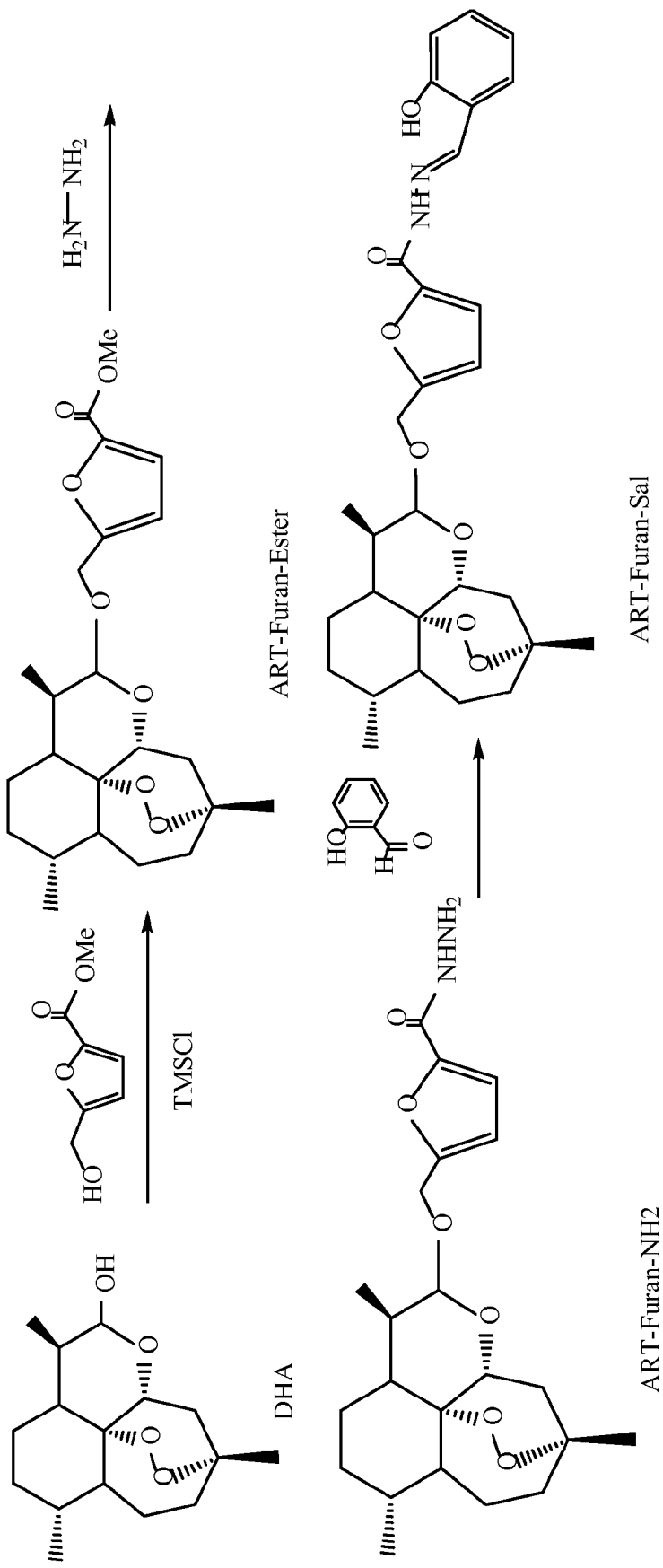
FIG. 2 shows the synthesis of a representative compound N'-(2-hydroxybenzylidene)-5-(dihydroxyartemisinin-methyl)-furan-2-carbohydrazide (ART-Furan-Sal)

N'-(2-hydroxybenzylidene)-5-(dihydroxyartemisinin-methyl)-furan-2-carbohydrazide (ART-Furan-Sal) was synthesized from methyl 5-(hydroxymethyl)-furan-2-carboxylate, methyl 5-(dihydroxyartemisinin-methyl)-furan-2-carboxylate (ART-Furan-Ester) as shown in FIG. 2.

Methyl 5-(hydroxymethyl)-furan-2-carboxylate. Methyl 5-(hydroxymethyl)-furan-2-carboxylate was synthesized according to procedure described in Raimundo, B. C., et al., *J. Med. Chem.*, 2004, 47 (12), 3111-3130). 5-formyl-2-furan carboxylic acid (1 g, 7.14 mmoles) was stirred in benzene (18 mL)/methanol (4 mL) in a 3-neck 50 mL round bottom flask with one neck connected to a funnel that was previously flushed with nitrogen gas. Trimethylsilyl diazomethane 2M in hexanes (3.6 mL, 7.2 mmoles) was added dropwise over a period of 15 min. After addition, the medium was a green limpid solution, which was stirred for 2 h at room temperature. The reaction advancement is monitored by TLC 8:2 Hexanes/AcOEt followed by 95:5 $CHCl_3$/MeOH, and stained with $KMnO_4$. Solvents were evaporated under vacuum, and 14 mL of methanol was added. The flask was placed in an ice-water bath and sodium borohydride (600 mg, 15.8 mmoles) was added. The reaction mixture was stirred for 3 h at room temperature. Water was poured off and the mixture extracted with AcOEt. The organic phase was dried over $MgSO_4$, and the solvent was evaporated. The product was purified by silica gel column chromatography (7×3.5 cm) with 100 mL of 90:10, then 200 mL of 80:20, and finally 400 mL of a 75:25 mixture of Hexane/AcOEt to yield a yellow powder after extraction (780 mg, 70%). NMR $^1$H 300 MHz, $CDCl_3$, (δ, ppm): 7.13 (d, J=3.4 Hz, 1H), 6.41 (d, J=3.3 Hz, 1H), 4.67 (d, J=6.2 Hz, 2H), 3.89 (s, 3H).

Methyl 5-(dihydroxyartemisinin-methyl)-furan-2-carboxylate (ART-Furan-Ester). DHA was introduced into a 100 mL 3-neck round bottom flask with one neck connected to nitrogen gas, that was previously heated under vacuum and flushed with $N_2$. The flask was flushed with cyclic vacuum/Nitrogen gas (1.261 g, 4.44 mmoles), before benzene (50 mL) the linker (833 mg, 5.34 mmoles in 5 mL benzene) were added. Using a funnel, TMSCl 1M in THF was added dropwise (2.24 mL, 2.24 mmoles). The solution became clear and was covered with aluminum foil for 3 h at r.t. The reaction was monitored by TLC using 8:2 Hexanes/AcOEt, and stained using $I_2$. Hydrolysis, with saturated NaOAc (DI water, 5 mL), changed the color of the solution from green to yellow/orange. The aqueous phase was extracted twice with AcOEt, and the organic phase was washed with 15 mL of NaCl sat, dried over $MgSO_4$, and the solvents evaporated. Hexane was added to the crude mixture. A white precipitate if it appears, is the unreacted DHA. The liquid phase was reddish. Purification was performed by silica gel column chromatography (7×3.5 cm), and using a 9:1 and then 8:2 mixture of Hexanes/AcOEt to elute the product. To separate the alpha product from the beta product, a second silica gel column chromatography was used (25×2.5 cm). Samples (10 mL fractions) were collected during elution with Hexanes/AcOEt: 250 mL 9:1 and then an 8:2 mixture of column solvents. The resulting powder was slightly yellow, which was washed with $Et_2O$ to give a white powder. A 1 h reaction lead to 33% mixture of beta product, 27% DHA, and 8% alpha product. A 3 h reaction was necessary to produce 70% beta linker product. $^1$H-NMR ($CDCl_3$) δ 0.86 (d, J=7.0 Hz), 0.94 (brs, 4H), 1.24 (m, 2H), 1.43 (brs, 4H), 1.60 (m, 3H), 1.87 (m, 1H), 2.02 (m, 1H), 2.37 (m, 1H), 2.64 (brs, 1H), 3.88 (s, 3H), 4.57 (d, J=12.9 Hz), 1H), 4.77 (d, J=13.4 Hz, 1H), 4.89 (brs, 1H), 5.45 (s, 1H), 6.40 (brs, 1H), 7.13 (brs, 1H); $^{13}$C-NMR ($CDCl_3$) δ 13.23, 20.72, 24.84, 25.06, 26.52, 31.13, 34.98, 36.79, 44.72, 52.25, 52.93, 62.12, 81.45, 88.43, 101.67, 104.53, 110.90, 119.12, 144.61, 156.57, 160.02.

5-(Dihydroxyartemisinin-methyl)-furan-2-carbohydrazide (ART-Furan-$NH_2$). ART-furan-OMe (40 mg, 95 μmoles) and methanol (5 mL) were added to a 10 mL round bottom flask with a condenser, that was previously flame-dried under vacuum and flushed with nitrogen gas. The system was under nitrogen pressure. Anhydrous hydrazine (40 μL, 1.3 mmoles) was added and the reaction mixture heated at reflux for 24 h. After evaporation under vacuum, the compound was purified by silica gel column chromatography (11×2 cm). Samples (8 mL) were collected and the column covered with aluminum foil. Elution solvents were 50 mL 99:1 Chloroform/Methanol, 50 mL 97:3, 50 mL 95:5. The reaction was monitored by TLC and the TLC products stained with ninhydrine in EtOH. A yellow powder was obtained (25 mg, 63%). $^1$H-NMR($C_6D_6$) δ 0.81 (m, 7H), 1.18 (m, 2H), 1.44 (m, 2H), 1.53 (brs, 1H), 1.57 (brs, 2H), 1.68 (m, 3H), 1.85 (m, 3H), 2.47 (dt, 1H), 2.87 (m, 1H) 3.95 (brs, 2H, exchangeable with D2O), 4.48 (m, 3H), 4.88 (d, J=3.0 Hz, 1H), 5.62 (brs, 1H), 6.04 (m, 1H), 7.15 (d, J=2.4 Hz, 1H), 8.2 (brs, 1H, exchangeable with $D_2O$); $^{13}$C-NMR($C_6D_6$) δ 12.72, 19.85, 20.17, 24.55, 24.97, 25.93, 30.93, 31.56, 34.30, 24.55, 36.48, 37.32, 44.50, 46.47, 52.50, 61.93, 80.67, 81.32, 87.88, 101.69, 104.21, 110.89, 114.85, 147.56, 153.90, 158.9.

N'-(2-hydroxybenzylidene)-5-(Dihydroxyartemisinin-methyl)-furan-2-carbohydrazide (ART-Furan-Sal). In a flame dried and $N_2$ flushed 5 mL round bottom flask is dissolved ART-Furan-$NH_2$ (23 mg, 54.4 μmoles) with Methanol (3 mL). Salicylaldehyde (15 μL, 150 μmoles) is added dropwise. The reaction is stirred 1 h to 24 h; disappearance of starting material is monitored with TLC 94:6 $CHCl_3$/MeOH ($R_f$ product 0.67). The solvent is evaporated under vacuum. The crude mixture is purified through a silica gel chromatography (1×7) cm with $CHCl_3$ (5 mL), and then 98:2 $CHCl_3$/MeOH (15 mL) to afford a fluffy red powder (25 mg, 87%). NMR $^1$H 300 MHz, $CDCl_3$ (δ, ppm): 10.99 (b, 1H), 9.67 (b, 1H), 8.59 (b, 1H), 7.33-7.20 (m, 2H), 6.99-93 (broad d, J=13.8 Hz, 1H), 6.90-6.87 (broad t, J=0.9 Hz, 1H), 6.46 (d, J=3.3 Hz, 1H), 5.46 (m, 1H), 4.90 (d, J=3.3 Hz, 1H), 4.66 (q, J=7.8 Hz, 2H), 2.75-2.60 (m, 1H), 2.45-2.35 (m, 1H), 2.10-2.05 (m, 1H), 1.93-1.85 (m, 1H), 1.80-1.55 (m, 3H), 1.50-1.35 (m, 5H), 1.26-1.17 (m, 3H), 0.96-0.87 (7H). NMR $^{13}$C 75.45 MHz, $CDCl_3$ (δ, ppm): 158.6, 146.1, 132.0, 130.9, 119.4, 117.5, 117.3, 111.6, 104.4, 101.9, 88.1, 81.0, 62.1, 52.5, 44.3, 37.5, 36.4, 34.5, 30.8, 26.2, 24.7, 24.5, 20.3, 12.9.

Example 2

Synthesis of N'-(2-hydroxybenzylidene)-1-(dihydroxyartemisinin-ethyl)-1H-1,2,3-triazole-4-carbohydrazide (ART-Triazole-Sal)

Figure 3:
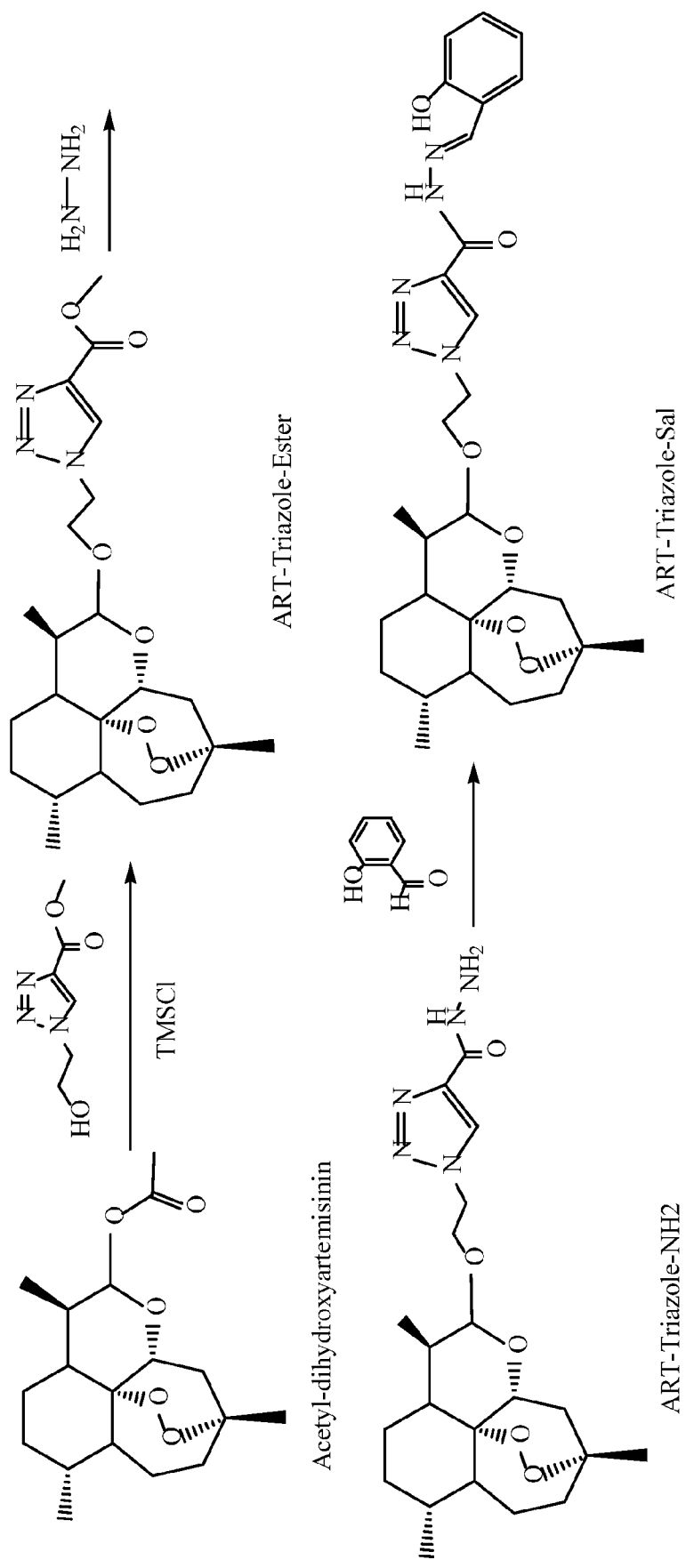
FIG. 3 shows the synthesis of a representative compound N'-(2-hydroxybenzylidene)-1-(dihydroxyartemisinin-ethyl)-1H-1,2,3-triazole-4-carbohydrazide (ART-Triazole-Sal)

N'-(2-hydroxybenzylidene)-1-(dihydroxyartemisinin-ethyl)-1H-1,2,3-triazole-4-carbohydrazide (ART-Triazole-Sal) was sequentially synthesized from 2-Azido ethanol: Methyl 1-(2-hydroxyethyl)-1H-1,2,3-triazole-4-carboxylate, Methyl 1-(Dihydroxyartemisinin-ethyl)-1H-1,2,3-triazole-4-carboxylate: DHA-Triazole-Ester, as shown in FIG. 3.

2-Azido ethanol. 2-Azido ethanol (Synthesis 1996, 11, 1345-49) was prepared as described below. 2-chloroethanol (2 mL, 30 mmoles) was rapidly added to a round bottom flask with a condenser containing sodium azide (2.34 g, 36 mmoles). The reaction mixture was heated to 30° C. for 1 h, and then 70° C. for 24 h. After a slow cool down to room temperature, the solution was extracted with diethylether. The organic phase was dried over $MgSO_4$ and the solvent evaporated to provide a colorless oil (1.882 g, 75%, d=1.149) and stored at 4° C. (slow decomposition was noted when stored at room temperature.). IR (DCM) cm$^{-1}$: 2125 $N_3$. NMR $^1$H 300 MHz, $CHCl_3$, (δ, ppm): 3.73 (m, 2H, $CH_2OH$), 3.38 (m, 2H $CH_2N$), 2.95 (b, 1H OH).

Methyl 1-(2-hydroxyethyl)-1H-1,2,3-triazole-4-carboxylate. Methyl 1-(2-hydroxyethyl)-1H-1,2,3-triazole-4-carboxylate was synthesized according to the procedure described by Tsypin, G. I.; Timofeeva, T. N., Mel'nikov, V. V.; Gidaspov, B. V. Zh. Org. Khim., 1977, 13, 2275-2281). Azidoethanol (1 mL, 13.2 mmoles) and methylpropiolate (5 mL, 56.25 mmoles) were added to a 50 mL round bottom flask and mixed for 4 days at room temperature. A beige powder was obtained after drying under vacuum (2.43 g, quant.). NMR 1H 300 MHz, $CHCl_3$, (δ, ppm): 8.21 (s, 1H), 4.52 (t, J=4.8 Hz, 2H, $CH_2N$), 4.08 (q, J=1.8 Hz and 4.2 Hz, 2H, $CH_2OH$), 3.89 (s, 3H).

Methyl 1-(Dihydroxyartemisinin-ethyl)-1H-1,2,3-triazole-4-carboxylate (ART-Triazole-Ester). Acetyl-dihydroxyartemisinin (50 mg, 0.154 mmole) in dry chloroform (0.5 mL) and the linker (32 mg, 0.187 mmole) were placed in a 2 mL round bottom flask that was previously flame-dried and flushed with nitrogen gas. The flask was placed in an ice-water bath and chloro trimethylsilane (25 μL, 0.197 mmole) was added dropwise. The reaction was maintained at 0° C. for 1 h, allowed to reach room temperature, and the flask was covered with aluminum foil. After 24 h, 0.5 mL of saturated sodium acetate was added. The organic phase was recovered and the aqueous phase extracted 2 times with chloroform. The organic phase was washed with brine and dried over $Na_2SO_4$ before the solvents were removed under vacuum. The crude product was purified by silica gel chromatography (1×3 cm) with 40 mL 7:3 Hexanes/AcOEt, which yielded a white powder after extracting oil product with diethyl ether (65 mg, 97%). NMR $^1$H 300 MHz, $CDCl_3$ (δ, ppm): 8.14 (s, 1H), 5.10 (s, 1H), 4.76 (d, J=3.3 Hz, 1H), 4.62 (m, 1H), 4.30 (m, 1H), 3.93 (s, 3H), 3.79 (m, 1H), 2.60 (m, 1H), 2.32 (m, 1H), 2.10-1.90 (m, 1H), 1.89-1.80 (m, 1H), 1.70-1.15 (m, 8H), 0.99-0.79 (m, 7H). NMR $^{13}$C 75.45 MHz, CDCl₃ (δ, ppm): 161.0, 139.5, 128.3, 104.2, 102.2, 87.8, 80.7, 66.1, 52.4, 52.2, 50.7, 44.0, 37.3, 36.3, 34.4, 30.6, 26.0, 24.6, 24.4, 20.3, 12.8.

1-(Dihydroxyartemisinin-ethyl)-1H-1,2,3-triazole-4-carbohydrazide (ART-Triazole-NH2). The ester (ART-Triazole-Ester) (15 mg, 34.3 μmoles), hydrazine hydrate (15 μL, 309 μmoles), and dry ethanol (0.5 mL) were placed in to a 5 mL round bottom flask that was previously flame dried and flushed with nitrogen. The flask was protected from light and the mixture stirred for 48 h at room temperature. The solvent was evaporated and the product purified by silica gel chromatography (1×5 cm), eluting with 98:2 chloroform/methanol, to yield a white powder (15 mg, Quant.). NMR $^1$H 300 MHz, CDCl₃ (δ, ppm): 8.28 (b, 1H), 8.11 (s, 1H), 5.11, (s, 1H), 4.75 (d, J=3.3 Hz, 1H), 4.64-4.59 (m, 2H), 4.35-4.28 (m, 1H), 4.04 (b, 2H), 3.83-3.76 (m, 1H), 2.62-2.57 (m, 1H), 2.32 (td, J=14.5 Hz and 3.9 Hz, 1H), 2.02-1.98 (m, 1H), 1.88-1.82 (m, 1H), 1.63-1.53 (m, 2H), 1.45-1.34 (m, 7H), 1.23-1.17 (m, 2H), 0.93-0.86 (m, 4H), 0.82-0.75 (m, 3H). NMR $^{13}$C 75.5 MHz, CDCl₃ (δ, ppm): 160.6, 141.7, 126.2, 104.2, 103.1, 102.0, 87.8, 65.9, 52.3, 50.7, 43.9, 37.3, 36.3, 34.3, 30.6, 26.0, 24.6, 24.3, 20.2, 12.8. ESI-MS positive (MeOH): 476.4 [M+K]⁺, 460.4 [M+Na]+(100%), 438.4 [M+H]⁺.

N'-(2-hydroxybenzylidene)-1-(Dihydroxyartemisinin-ethyl)-1H-1,2,3-triazole-4-carbohydrazide (ART-Triazole-Sal). Same procedure as ART-Fur-Sal. 46 mg of starting material affords a fluffy white powder (20 mg, 81%) after 24 h reaction. NMR $^1$H 300 MHz CDCl₃(δ, ppm): 11.10 (s, 1H), 10.45 (s, 1H), 8.51 (s, 1H), 8.36 (s, 1H), 7.33-7.24 (m, 2H), 7.00 (d, J=8.1 Hz, 1H), 6.90 (t, J=6.9 Hz, 1H), 5.09 (s, 1H), 4.76 (d, J=3.6 Hz, 1H), 4.69-4.65 (m, 2H), 4.35-4.33 (m, 1H), 3.85-3.78 (m, 1H), 2.62-2.55 (m, 1H), 2.40-2.20 (m, 1H), 2.05-1.13 (m, 15H), 0.93-0.71 (m, 7H). NMR $^{13}$C 75.5 MHz, CDCl₃ (δ, ppm): 158.6, 155.5, 151.0, 141.7, 132.0, 131.0, 127.5, 119.3, 117.5, 117.3, 104.2, 102.1, 87.8, 80.8, 65.9, 52.3, 50.9, 44.0, 37.4, 36.3, 34.3, 30.6, 26.0, 24.6, 24.4, 20.2, 12.8. ESI-MS positive (MeOH): 580.3 [M+K]⁺, 564.4 [M+Na]⁺, 542.4 [M+H]⁺ (100%).

Example 3

Synthesis of N'-(2-hydroxybenzylidene)-5-(dihydroxyartemisinin-methyl)-2-pyridine carbohydrazide (ART-Pyr-Sal)

Figure 4:
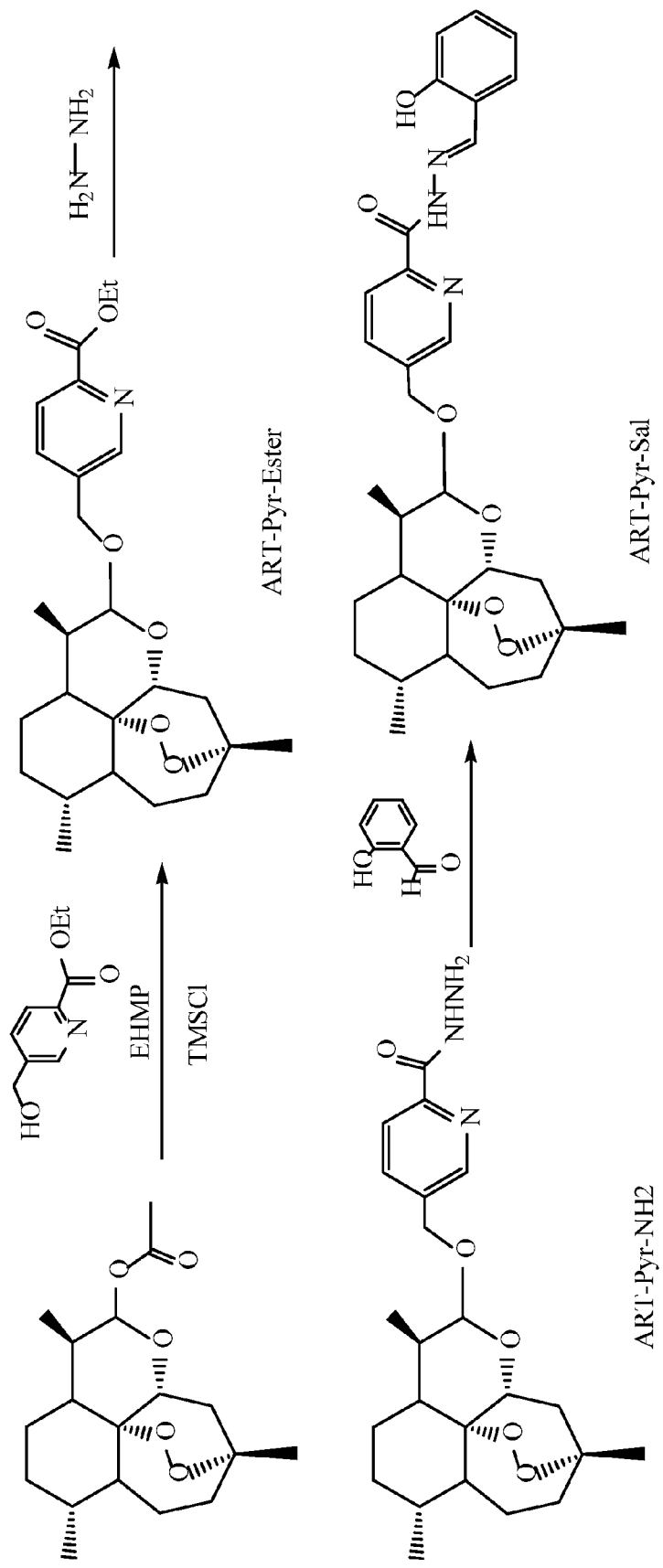
FIG. 4 shows the synthesis of a representative compound N'-(2-hydroxybenzylidene)-5-(dihydroxyartemisinin-methyl)-2-pyridine carbohydrazide (ART-Pyr-Sal)

N'-(2-hydroxybenzylidene)-5-(dihydroxyartemisinin-methyl)-2-pyridine carbohydrazide (ART-Pyr-Sal) was synthesized sequentially from dimethyl-2,5-pyridinedicarboxylate, pyridine 2,5-dicarboxylic acid 5-methyl ester, 5-hydroxymethyl-2 ethyl pyridinecarboxylate (EHMP), 5-(dihydroxyartemisinin-methyl)-2 ethyl pyridinecarboxylate (ART-Pyr-Ester) as shown in FIG. 4.

Dimethyl-2,5-pyridinedicarboxylate. The compound was synthesized from a procedures from Isagawa, K., et al., *Nippon Kagaku Zasshi*, 88(5), 553-6, 1967, Dawson, M. I., et al., *J. Med. Chem.* 26:1282-1293, 1983, and Hull, K. G., et al., *Tetrahedron* 53:12405-12414, 1997. 2,5-pyridinedicarboxylic acid (30 g, 0.182 moles) and methanol (300 mL) were mixed together in a 1 L round bottom flask connected to a funnel containing sulfuric acid conc. (16 mL, 0.285 moles). The acid was added dropwise over a period of 30 min, and then the funnel was removed and replaced with a condenser. The mixture was heated at reflux for 16 h which becomes a brown and later a yellow solution. After the reaction cooled to r.t., the slurry was poured in 500 mL of ice water. Sodium bicarbonate solid (30 g) was added to neutralize the pH. The reaction mixture was concentrated with evaporation in a vacuum. The slurry was dissolved with water/chloroform and the compound processed by extraction. The organic layer was dried with brine and then MgSO₄ before solvents were evaporated under reduced pressure to yield a pale yellow solid (29.05 g, 83%). NMR $^1$H 300 MHz, CDCl₃ (δ, ppm): 9.29 (dd, J=1.5 Hz and 0.6 Hz, 1H, CH), 8.42 (dd, J=6 Hz and 2.1 Hz, 1H, CH), 8.19 (dd, J=7.2 Hz and 0.9 Hz, 1H, CH), 4.02 (s, 3H, CH₃), 3.97 (s, 3H, CH₃).

Pyridine 2,5-dicarboxylic acid 5-methyl ester. Pyridine 2,5-dicarboxylic acid 5-methyl ester was synthesized according to the procedure described by Faul, M. M., et al., (*J. Org. Chem.* 66, 5772-5782, 2002). Di-ester (28 g, 0.146 moles) and methanol (260 mL) were stirred in a 500 mL 3-neck round bottom flask with connected a condenser and a funnel. The reaction mixture was heated at reflux after adding one portion of NaOH (6.2 g, 0.155 moles) for 3 h 30 min to produce a white mixture. While at reflux, 2M HCl (121 mL) was added dropwise over a 1 h period to produce a yellow solution. The flask was placed in an ice water bath to cool, and at r.t., a precipitate appears. The precipitate was collected by filtration and washed with 2:1 MeOH/H₂O (35 mL) and then water (50 mL). The precipitate was dried overnight. The final yield was 19.68 g (75%). NMR $^1$H 300 MHz, DMSO-d₆ (δ, ppm): 9.12 (m, 1H), 8.40 (dd, J=2.1 Hz and 8.1 Hz, 1H, CH), 8.12 (dd, J=0.9 Hz and 8.4 Hz, 1H, CH), 3.89 (s, 3H, CH₃). NMR $^{13}$C 75.45 MHz, DMSO-d₆ (δ, ppm): 165.9, 165.0, 152.1, 150.2, 138.8, 128.3, 125.0, 53.2.

5-Hydroxymethyl-2 ethyl pyridinecarboxylate (EHMP). The monoester was converted to the corresponding Ca-salt, and then reduced with sodium borohydride to give 5-Hydroxymethyl-2 ethyl pyridinecarboxylate (EHMP). NMR $^1$H 300 MHz, CDCl₃ (δ, ppm): 8.63 (b, 1H), 8.05 (broad d, J=7.86 Hz, 1H, CH), 7.83 (dd, J=2.0 Hz and 8.0 Hz, 1H, CH), 4.79 (s, 2H, CH₂), 4.42 (q, J=7.1 Hz, CH₂), 1.40 (t, J=7.1 Hz, 3H, CH₃). NMR $^{13}$C 75.45 MHz, CDCl₃ (δ, ppm): 165.0, 148.1, 146.6, 140.8, 135.4, 124.9, 61.9, 61.8, 14.3.

5-(Dihydroxyartemisinin-methyl)-2 ethyl pyridinecarboxylate (ART-Pyr-Ester). EHMP was then coupled to dihydroartemisinin by the same procedure as described in Example 6 to give 5-(dihydroxyartemisinin-methyl)-2 ethyl pyridinecarboxylate (ART-Py-ester). The reaction time was 48 h and the yield was 39%. NMR $^1$H 300 MHz, CDCl₃ (δ, ppm): 8.69 (b, 1H), 8.07 (broad d, J=7.9 Hz, 1H, CH), 7.71 (dd, J=2.2 Hz and 8.1 Hz, 1H, CH), 5.39 (s, 1H, CH), 4.97 (d, J=13.4 Hz, 1H, CH₂), 4.88 (d, J=3.3 Hz, 1H, CH), 4.57 (d, J=13.4 Hz, 1H, CH₂), 4.43 (q, J=7.2 Hz, CH₂), 2.71-2.61 (m, 1H, CH), 2.38-2.28 (m, 1H, CH), 2.04-1.16 (several m, 16H), 0.93-0.84 (m, 7H). NMR $^{13}$C 75.45 MHz, CDCl₃ (δ, ppm): 165.1, 148.6, 147.4, 137.5, 135.4, 124.7, 104.2, 101.9, 88.0, 80.9; 67.1, 61.9, 52.4, 44.2, 37.4, 36.3, 34.5, 30.8, 26.1, 24.6, 24.5, 20.2, 14.3, 13.0.

5-(Dihydroxyartemisinin-methyl)-2-pyridine carbohydrazide (ART-Pyr-NH₂). ART-Pyr-ester was then reacted with hydrazine to obtain the title compound 5-(dihydroxyartemisinin-methyl)-2-pyridine carbohydrazide. Yield was 83%. ESI-MS positive (MeOH): 472.4 [M+K]⁺, 456.4 [M+Na]⁺, 434.4 [M+H]⁺, 418.6 [M+H—NH₂]+(100%).

N'-(2-hydroxybenzylidene)-5-(dihydroxyartemisinin-methyl)-2-pyridine carbohydrazide (ART-Pyr-Sal). Same procedure as ART-Fur-Sal. 46 mg of starting material affords a fluffy white powder (52 mg, 91%) after 24 h reaction. NMR $^1$H 300 MHz, CDCl₃ (δ, ppm): 11.10 (s, 1H), 10.90 (s, 1H), 8.52 (d, J=1.5 Hz, 1H), 8.50 (s, 1H), 8.24 (s, J=7.8 Hz, 1H), 7.83 (dd, J=1.8 Hz and 8.1 Hz, 1H), 7.30-7.22 (m, 2H), 7.02 (d, J=8.1 Hz, 1H), 6.90 (t, J=7.5 Hz, 1H), 5.43 (s, 1H), 4.95 (d, J=13.2 Hz, 1H, CH₂), 4.92 (d, J=3.3 Hz, 1H), 4.61 (d, J=13.2 Hz, 1H, CH₂), 3.75-2.65 (m, 1H), 2.45-2.32 (m, 1H), 2.05-2.0

(m, 1H), 1.98-1.25 (m, 12H), 0.97-0.93 (m, 7H). NMR $^{13}$C 75.5 MHz, CDCl$_3$ (d, ppm): 159.6, 158.7, 151.2, 148.0, 147.0, 137.8, 136.3, 132.0, 131.0, 122.6, 119.3, 117.5, 117.3, 104.3, 102.0, 88.1, 81.0, 67.1, 52.5, 44.3, 37.5, 36.4, 34.5, 30.8, 26.1, 24.7, 24.6, 20.3, 13.0. ESI-MS positive (MeOH): 576.3 [M+K]$^+$, 560.4 [M+Na]+(100%), 538.4 [M+H]$^+$.

Example 4

Synthesis Of N'-(2-hydroxybenzylidene)-4-(dihydroxyartemisinin-methyl)-phenyl carbohydrazide (ART-Phe-Sal)

N'-(2-hydroxybenzylidene)-4-(dihydroxyartemisinin-methyl)-phenyl carbohydrazide (ART-Phe-Sal) was synthesized from 4-[(10-dihydroartemisininoxy)-methyl]benzoate as shown in FIG. 5.

4-(Dihydroxyartemisinin-methyl)phenyl carbohydrazide (ART-Phe-NH$_2$). This compound was prepared by the reported procedure according to Lai, Sasaki, Singh and Massey *Life Sciences* 2005, 76, 1267-29. Hydrazine anhydrous (0.2 mL, 6.3 mmol) with stirring at room temperature for 3 hr was added to a solution of 4-[(10-dihydroartemisininoxy)-methyl]benzoate of artemisinin (16) (325 mg, 0.75 mmol) in methanol (2 mL). Water (10 mL) was added to the reaction mixture and extracted with CHCl$_3$. The combined organic extracts were dried over MgSO$_4$, concentrated, and the crude product was purified by flash column chromatography using methanol/CHCl$_3$ (0:100 to 4:96) to give the final artelinic acid hydrazide (245 mg, 75.5%). $^1$H NMR (CDCl$_3$) δ 7.72 (d, 2H), 7.39 (d, 2H), 5.45 (s, 1H), 4.90 (m, 2H), 4.56 (d, 1H), 2.68 (m, 1H), 2.35 (dt, 1H), 2.02 (m, 1H), 1.88 (m, 1H), 1.81 (m, 2H), 1.62 (m, 1H), 1.46 (brs, 4H), 1.23 (m, 2H), 0.95 (m, 7H). IR: 3318.6 cm$^{-1}$ (CO—NH). ESI-MS: m/z [M+H]$^+$ 433.23.

N'-(2-hydroxybenzylidene)-4-(dihydroxyartemisinin-methyl)-phenyl carbohydrazide (ART-Phe-Sal). Same procedure as ART-Fur-Sal. 0.1 g of starting material affords a fluffy white powder (0.1 g, 97%) after 24 h reaction. ESI-MS positive (MeOH): 536 [M+H]$^+$.

Example 5

Synthesis of N'-(benzylidene)-4-(dihydroxyartemisinin-methyl)-phenyl carbohydrazide (ART-Phe-Bz)

N'-(benzylidene)-4-(dihydroxyartemisinin-methyl)-phenyl carbohydrazide (ART-Phe-Bz) was synthesized from 4-(dihydroxyartemisinin-methyl)-phenyl carbohydrazide (ART-Phe-NH$_2$) as shown in FIG. 6.

Same procedure as ART-Fur-Sal. 0.1 g of starting material affords a fluffy white powder (0.1 g, 97%) after 24 h reaction. ESI-MS positive (MeOH): 520 [M+H]$^+$.

Example 6

Synthesis of N'-(5-hydroxy-3-hydroxymethyl-2-methyl-4-pyridylidene)-4-(dihydroxyartemisinin-methyl)-phenyl carbohydrazide (ART-Phe-Pyridoxal)

N'-(5-hydroxy-3-hydroxymethyl-2-methyl-4-pyridylidene)-4-(dihydroxyartemisinin-methyl)-phenyl carbohydrazide (ART-Phe-Pyridoxal) was synthesized from ART-Phe-NH2 as shown in FIG. 7.

Same procedure as ART-Fur-Sal. 0.1 g of starting material affords a fluffy white powder (0.09 g, 90%) after 24 h reaction. ESI-MS positive (MeOH): 581 [M+H]$^+$.

Example 7

Synthesis of N'-(2-hydroxybenzylidene)-(2E)-methyl-4-dihydroartemisin-2-butenoic hydrazide (ART-Butenoic-Sal)

N'-(2-hydroxybenzylidene)-(2E)-methyl-4-dihydroartemisin-2-butenoic hydrazide (ART-Butenoic-Sal) was synthesized from (2E)-methyl-4-hydroxy-2-butenoate as shown in FIG. 8.

(2E)-Methyl-4-dihydroartemisin-2-butenoate (ART-Butenoic-ester). In a 100 mL 3-neck round bottom flask with one neck connected to nitrogen gas, prior heated under vacuum and flushed with N$_2$, DHA is introduced and flushed with cyclic vacuum/Nitrogen gas (1.261 g, 4.44 mmoles), Benzene (50 mL) is added and then is added (2E)-Methyl-4-hydroxy-2-butenoate (619 mg, 5.34 mmoles in 5 mL benzene). Using a funnel TMSCl 1M in THF is added dropwise (2.24 mL, 2.24 mmoles). The solution becomes clear and is covered with an aluminum foil for 3 h at room temperature. The reaction advancement is monitored by TLC: 8:2 Hexanes/AcOEt then stained by I$_2$. Hydrolysis, with saturated NaOAc (DI water, 5 mL), changes color solution from green to yellow/orange. The aqueous phase is extracted 2 times with AcOEt, and then the organic phase is washed with 15 mL of NaCl sat, then dried over MgSO$_4$ and evaporated. Hexane is added to the crude mixture if a white precipitate appears, it is the unreacted DHA, and the liquid phase is reddish. Purification through a silica gel column chromatography (7×3.5 cm) eluted with 9:1 then 8:2 mixture of Hexanes/AcOEt. The yield was 70%.

(2E)-Methyl-4-dihydroartemisin-2-butenoic hydrazide (ART-Butenoic-NH$_2$). In a 10 mL round bottom flask, flame dried under vacuum and then flushed with nitrogen gas, with a condenser is introduced the methyl ester (36 mg, 95 μmoles) and methanol (5 mL). The system is under nitrogen pressure. The anhydrous hydrazine (40 μL, 1.3 mmoles) is added and the reaction mixture is heated at reflux for 24 h. After evaporation with vacuum, purification is made by a silica gel column chromatography (11×2 cm). The yield was 63%.

N'-(2-hydroxybenzylidene)-(2E)-Methyl-4-dihydroartemisin-2-butenoic hydrazide (ART-Butenoic-Sal). In a flame dried and N$_2$ flushed 5 mL round bottom flask is dissolved the hydrazide (21 mg, 54.4 μmoles) with methanol (3 mL). Salicylaldehyde (15 μL, 150 μmoles) is added dropwise. The reaction is stirred 1 h to 24 h; disappearance of starting material is monitored with TLC 94:6 CHCl$_3$/MeOH (R$_f$ product 0.67). The solvent is evaporated under vacuum. The crude mixture is purified through a silica gel chromatography (1×7) cm with CHCl$_3$ (5 mL), and then 98:2 CHCl$_3$/MeOH (15 mL). The yield was 87%.

Example 8

Synthesis of N'-(2-hydroxybenzylidene)-methyl-4-dihydroartemisin-2-butynoic hydrazide (ART-Butynoic-Sal)

N'-(2-hydroxybenzylidene)-methyl-4-dihydroartemisin-2-butynoic hydrazide (ART-Butynoic-Sal) was synthesized from dihydroartemisinin and methyl-4-hydroxy-2-butynoate as shown in FIG. 9.

Starting from dihydroartemisinin and methyl 4-hydroxy-2-butynoate, the synthesis of ART-Butynoic-Sal is similar to the synthetic procedure for N'-(2-hydroxybenzylidene)-(2E)-Methyl-4-dihydroartemisin-2-butenoic hydrazide (ART-Butenoic-Sal) outlined above.

Example 9

Synthesis of 4-(dihydroxyartemisinin-methyl)-phenyl carbohydrazide (Dimer-Sal)

4-(Dihydroxyartemisinin-methyl)-phenyl carbohydrazide (Dimer-Sal) was synthesized as shown in FIG. 10.

Synthesis of Dimer-CONHNH$_2$. A solution of dimer-COOH (17 mg, 27 µmol) in a dried dichloromethane-DMSO (20:1=1 mL) was modified by addition of EDCI (12.4 mg, 65 µmol) and tetrafluorophenol (10.6 mg, 64 µmol) in the presence of Et$_3$N (20 µL). The reaction was stirred for 1 h at room temperature, the mixture then treated with an excess of anhydrous hydrazine (10 µL). The reaction was kept standing for 3 h. The product was purified by short silica gel column chromatography, and the product eluted with chloroform, followed by chloroform-methanol (20:1). The product-containing fractions were combined, and concentrated under reduced pressure to yield 13 mg of a mixture of dimer-COOH and the corresponding hydrazide (dimer-CONHNH$_2$). The ratio of the two trioxane dimers was determined to be 1:1, based on the integrals of $^1$H-NMR of the reaction product. 300 MHz $^1$H NMR (CDCl$_3$) δ 7.03 (s, 1H), 5.30 (s, 1H), 5.17 (s, 1H), 4.20-4.05 (m, 2H), 1.43, (s), 1.39 (s), 0.93 (d, J=6.0, 6H), 0.84 (d, J=7.6, 6H); LRMS (ES) m/z=657.6 (M+Na$^+$).

Dimer-Sal. DimerCONHNH$_2$ (1 eq) and salicylaldehyde (1.2 eq) are mixed in methanol. The reaction mixture is kept stirring at room temperature for 2 hrs. The TLC should show the disappearance of artelinic acid hydrazine, and the appearance of a new spot that is the desired hydrazone.

Example 10

Evaluation of Anti-Cancer Activities of a Representative Compound ART-Phe-Sal Representative compound of the invention, ART-Phe-Sal, was subjected to the evaluation for their effects on Molt-4 human leukemia cells, normal human lymphocytes, and DAOY medulloblastoma cells.

Molt-4-lymphoblastoid cells were purchased from the American Type Culture Collection (Rockville, Md.). They are acute lympoblastic leukemia cells from human peripheral blood. Cultures were maintained in RPMI-1640 (Gibco, Long Island, N.Y.) supplemented with 10% fetal bovine serum (Hyclone, New Haven, Conn.). Cells were cultured at 37° C. in 5% CO$_2$/95% air and 100% humidity, and were split 1:2 at a concentration of approximately $1 \times 10^6$/mL. Approximate cell numbers before experiment were between $150 \times 10^3$ to $300 \times 10^3$ per mL.

Normal human lymphocytes were isolated from fresh blood obtained from a healthy donor and isolated using a modification of the Ficoll-hypaque centrifugation method disclosed by Boyum, A., "Isolation of Mononuclear Cells and Granulocytes from Human Blood," *Scand. Clin. Lab. Invest.* 21:77-89 (1968). In this method, 20-100 µl of whole blood obtained from a finger prick was mixed with 0.5 ml of ice-cold RPMI-1640 without phenol red (GIBCO, N.Y.) in a 1.5 ml heparinized microfuge tube (Kew Scientific Inc., Columbus, Ohio). Using a Pipetman, 100 µl of cold lymphocyte separation medium (LSM) was layered at the bottom of the tube. The samples were centrifuged at 3500 rpm for 2 min in a microfuge (Sorvall, Microspin model 245) at room temperature. The lymphocytes in the upper portion of the Ficoll layer were pipetted out. Cells were washed twice in 0.5 ml RPMI-1640 by centrifugation for 2 min at 3500 rpm in the microfuge. The final pellet consisting of approximately $0.4$-$2.0 \times 10^5$ lymphocytes was resuspended in RPMI-1640. Cell viability was determined before experiments using trypan blue exclusion and found to be more than 95%.

Molt-4-lymphoblastoid cells and normal human lymphocytes were aliquoted in 0.1 mL volumes into microfuge tubes. Human holotransferrin (Sigma Chemicals, St. Louis, Mo.) was added to samples of the cells. Different concentrations of freshly prepared dihydroartemisinin dissolved in complete medium were added 1 hr later to the tubes. The final concentration of holotransferrin was 12 µM and dihydroartemisinin was either 1, 10, 50, or 200 µM. Equal volume of medium was added to control samples (i.e., samples without holotransferrin or dihydroartemisinin). Cells were kept in an incubator at 37° C. under 5% CO$_2$ and 95% air during the experiment. At 1, 2, 4, and 8 hrs after the addition of dihydroartemisinin, the cell number was counted from a 10 µl aliquot from the samples using a hemocytometer. The cells were thoroughly mixed by repeated pipeting before an aliquot was taken for counting. In the case of Molt-4 cells, cell viability was not determined because it is not correlated with cell loss as rapid cell disintegration was observed.

Data are expressed as percentage of cell count at a certain time point compared to cell count at the time when dihydroartemisinin was added as shown in FIG. 11. Time-response curves were compared by the method of Krauth, J., "Nonparametric Analysis of Response Curves," *J. Neurosci. Method* 2:239-252, 1980.

FIG. 11 compares the effects of ART-Phe-Sal, DHA, and artemisinin-tagged holotransferrin (ART-Tf) on Molt-4 human leukemia cell. Different concentrations of the compounds ([ART-Phe-Sal]=10 mM, [DHA]=10 µM, and [ART-Tf]=12 µM) were added to cell cultures at time zero and cells were counted at different times interval. The compound ART-Phe-Sal was more potent than either dihydroartemisinin (DHA) or artemisinin-tagged holotransferrin (ART-Tf) under the assay condition.

FIG. 12 shows the effect of ART-Phe-Sal on normal human lymphocytes. Different concentrations of the compounds ([ART-Phe-Sal]=10 µM, [ART-Phe-Sal]=20 µM, [ART-Phe-Sal]=50 mM, and [ART-Phe-Sal]=100 mM) were added to cell cultures at time zero and cells were counted at different times interval. FIG. 12 indicates that the compound ART-Phe-Sal was relatively non-toxic to normal human lymphocytes.

The compound ART-Phe-Sal was tested on DAOY medulloblastoma cells using the MTT assay. DAOY Medulloblastoma cells (5,000 cells/200 µL) was seeded on a 96 well plate and incubated for 24 h at 37° C. Cell culture medium was removed after 24 h and 150 µL of medium with treatment was added. Each experimental treatment had holo-Tf (20 µg/well). Treatment assay was viewed under light microscope after 24 h. Impressive cell shrinkage was seen across all DHA treatments. Moderate cell shrinkage was observed in holo-Tf, and ART-Phe-Sal treatments.

Figure 13:
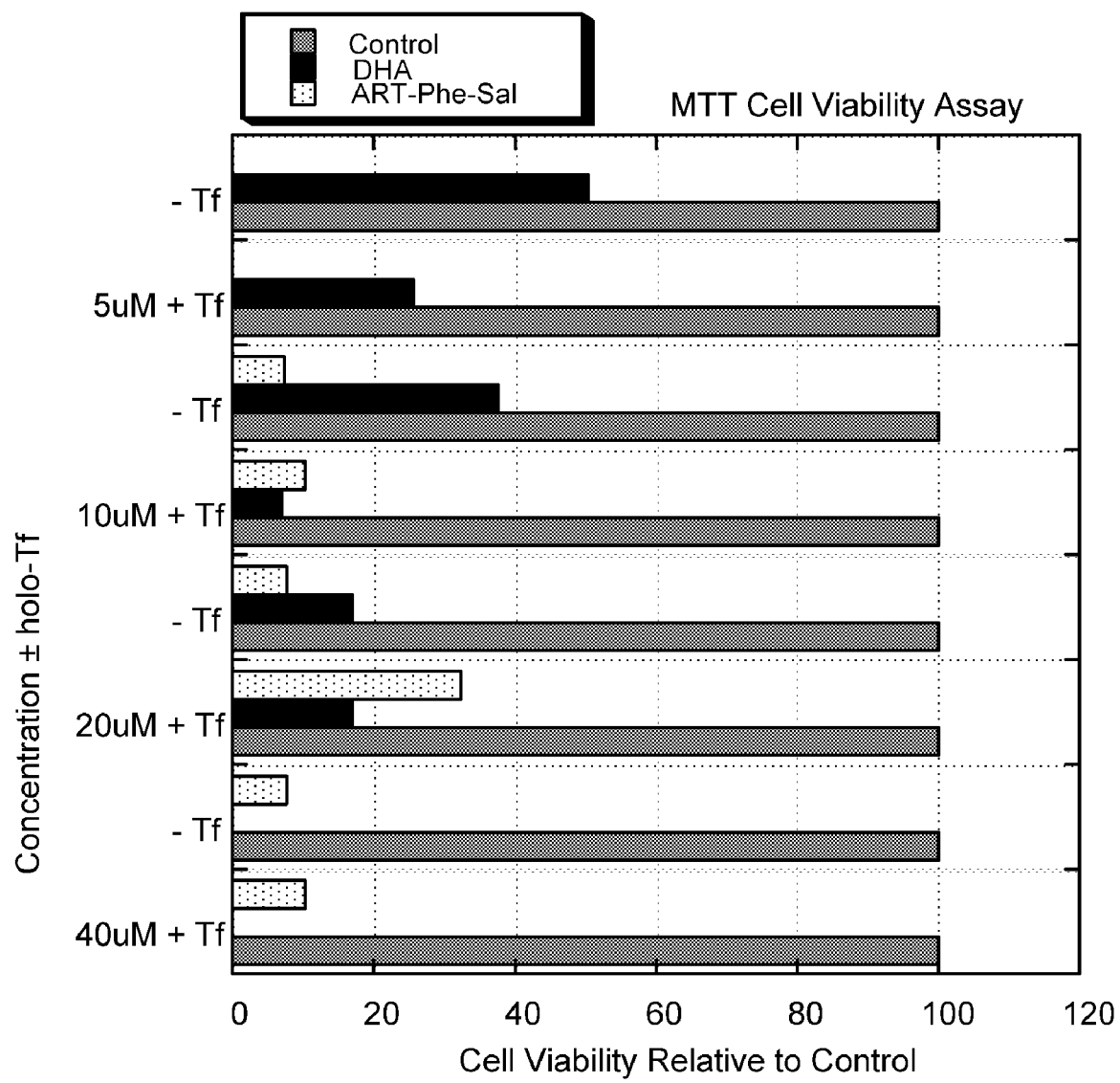
FIG. 13 compares the effect of ART-Phe-Sal and DHA on DAOY medulloblastoma cells.

Treatment medium was removed after 48 h, and 100 µL of cell medium was added. MTT Reagent (10 µL, 12 mM) was added to each well. This solution was incubated at 37° C. for 4 h. Isopropanol (100 µL) was added to each well to lyse the cells, which were then incubated at 4° C. for 30 m. After incubation each well was plunged (3×200 µL) to ensure the cells were lysed. The incubated medium with MTT reagent was then centrifuged at 13,000 RPM in an eppendorph centrifuge for 3 minutes at room temperature. 100 µL of supernatant was read in a plate reader at λ=570 nm. FIG. 13 compares the effect of dihydroartemisinin (DHA) and ART-Phe-Sal on DAOY medulloblastoma cell line. The concentration of holo-Tf was 1.7 µM.

Example 11

Evaluation of Anti-Cancer Activities of Representative Compounds Using DTP Human Tumor Cell Line Screen Representative compounds of the invention, prepared as described in EXAMPLES 1-6, were submitted to the Developmental Therapeutics Program of the United States National Cancer Institute (NCI) to screen for anti-cancer activity. The anti-cancer activities of the six compounds were tested against approximately 60 human tumor cell lines representing leukemia, melanoma, and cancers of the lung, colon, breast, ovary, kidney, prostate, and brain. The following screening methodology was provided by the NCI.

The human tumor cell lines of the cancer screening panel were grown in RPMI 1640 medium containing 5% fetal bovine serum and 2 mM L-glutamine. For experimental screens, cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% carbon dioxide, 95% air and 100% relative humidity for 24 hours prior to addition of the compounds.

After 24 hours of incubation, two plates of each cell line were fixed in situ with trichloroacetic acid (TCA) to represent a measurement of the cell population for each cell line at the time of compound addition (Tz). The compounds were solubilized in dimethyl sulfoxide at 400-fold the desired final maximum test concentration and stored frozen prior to use. At the time of drug addition, frozen aliquots of the compounds thawed and diluted with complete medium containing 50 μg/ml gentamicin. Aliquots of 100 μl of these different compound dilutions were added to the appropriate microtiter wells already containing 100 μl of medium, resulting in the required final compound concentration of 10 μM.

Following compound addition, the plates were incubated for an additional 48 h at 37° C., 5% carbon dioxide, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the three absorbance measurements [time zero, (Tz), control growth, (C), and test growth in the presence of compound (Ti)], the percentage growth was calculated at each of the compound concentrations levels. Percentage growth inhibition was calculated with the following algorithms:

[(Ti−Tz)/(C−Tz)]×100 for concentrations for which Ti>/=Tz

[(Ti−Tz)/Tz]×100 for concentrations for which Ti<Tz

The results of the NCI in vitro anticancer screening with six compounds against various human tumor cell lines are presented below in Tables 2-7. In the tables, columns 1 and 2 indicate the panel and cell line, and column 3 indicates the percent of cell growth following incubation with the subject compound. The growth percent mean, delta, and range for each compound are given below.

TABLE 2

Compound: ART-Phe-Bz

| Panel | Cell Line | Growth Percent |
|---|---|---|
| Non-Small Cell Lung Cancer | EKVX | 16.45 |
| | HOP-62 | 52.14 |
| | HOP-92 | 2.94 |
| | NCI-H226 | 29.10 |
| | NCI-H23 | 30.10 |
| | NCI-H322M | 53.20 |
| | NCI-H460 | 32.58 |
| | NCI-H522 | −9.33 |
| Colon Cancer | COLO 205 | 17.72 |
| | HCC-2998 | 22.05 |
| | HCT-116 | 5.59 |
| | HCT-15 | 16.27 |
| | HT29 | 18.46 |
| | KM12 | 10.19 |
| | SW-620 | 19.48 |
| Breast Cancer | BT-549 | 14.60 |
| | HS 578T | 34.12 |
| | MCF7 | 11.63 |
| | MDA-MB-231/ATCC | 26.78 |
| | MDA-MB-435 | 12.48 |
| | NCI/ADR-RES | 19.93 |
| | T-47D | 11.51 |
| Ovarian Cancer | OVCAR-3 | 11.56 |
| | OVCAR-4 | 18.29 |
| | OVCAR-5 | 28.19 |
| | OVCAR-8 | 26.65 |
| | SK-OV-3 | 53.03 |
| Leukemia | CCRF-CEM | 6.71 |
| | HL-60(TB) | −49.40 |
| | K-562 | 7.86 |
| | MOLT-4 | −25.73 |
| | RPMI-8226 | 1.50 |
| | SR | −24.04 |
| Renal Cancer | 786-0 | 26.79 |
| | A498 | 30.47 |
| | ACHN | 16.91 |
| | CAKI-1 | 5.53 |
| | SN12C | 23.38 |
| | TK-10 | 19.78 |
| | UO-31 | −21.11 |
| Melanoma | LOX IMVI | 8.89 |
| | M14 | 34.29 |
| | MALME-3M | 32.27 |
| | SK-MEL-2 | −3.22 |
| | SK-MEL-28 | 45.74 |
| | SK-MEL-5 | 2.01 |
| | UACC-257 | 25.96 |
| | UACC-62 | 24.51 |
| Prostate Cancer | PC-3 | 12.32 |
| CNS Cancer | SF-268 | 35.30 |
| | SF-295 | 14.30 |
| | SF-539 | 25.70 |
| | SNB-19 | 51.29 |
| | SNB-75 | 0.39 |
| | U251 | 36.35 |

The mean growth percent for ART-Phe-Bz is 17.28; the delta value is 66.68; and the range is 102.60.

TABLE 3

Compound: ART-Furan-Sal

| Panel | Cell Line | Growth Percent |
|---|---|---|
| Non-Small Cell Lung Cancer | EKVX | 25.37 |
| | HOP-62 | 12.94 |
| | HOP-92 | 37.02 |
| | NCI-H226 | 13.93 |
| | NCI-H23 | 17.54 |

TABLE 3-continued

Compound: ART-Furan-Sal

| Panel | Cell Line | Growth Percent |
|---|---|---|
| | NCI-H460 | −26.28 |
| | NCI-H522 | −10.76 |
| Colon Cancer | COLO 205 | 18.60 |
| | HCC-2998 | 5.37 |
| | HCT-116 | 13.81 |
| | HCT-15 | 30.86 |
| | HT29 | 22.40 |
| | SW-620 | 13.95 |
| Breast Cancer | BT-549 | 22.47 |
| | HS 578T | 40.07 |
| | MCF7 | 1.18 |
| | MDA-MB-231/ATCC | 31.58 |
| | MDA-MB-435 | 25.70 |
| | NCI/ADR-RES | 11.14 |
| | T-47D | 10.28 |
| Ovarian Cancer | OVCAR-3 | 30.23 |
| | OVCAR-4 | 12.86 |
| | OVCAR-5 | 28.70 |
| | OVCAR-8 | 17.07 |
| | SK-OV-3 | 14.53 |
| Leukemia | CCRF-CEM | −23.63 |
| | HL-60(TB) | −43.79 |
| | K-562 | 8.79 |
| | MOLT-4 | −23.49 |
| | RPMI-8226 | 13.00 |
| | SR | −29.47 |
| Renal Cancer | 786-0 | −22.22 |
| | A498 | 12.88 |
| | ACHN | 7.80 |
| | CAKI-1 | 17.44 |
| | SN12C | 27.18 |
| | TK-10 | 40.77 |
| | UO-31 | −35.28 |
| Melanoma | LOX IMVI | 0.03 |
| | M14 | −48.54 |
| | SK-MEL-2 | −27.21 |
| | SK-MEL-28 | 16.46 |
| | SK-MEL-5 | −46.62 |
| | UACC-257 | 9.72 |
| | UACC-62 | −5.97 |
| Prostate Cancer | PC-3 | 28.01 |
| CNS Cancer | SF-268 | −0.43 |
| | SF-295 | 12.70 |
| | SF-539 | −11.48 |
| | SNB-19 | 25.11 |
| | SNB-75 | −17.31 |
| | U251 | 12.24 |

The mean growth percent for ART-Furan-Sal is 6.1; the delta value is 54.64; and the range is 89.31.

TABLE 4

Compound: ART-Triazole-Sal

| Panel | Cell Line | Growth Percent |
|---|---|---|
| Non-Small Cell Lung Cancer | EKVX | 35.04 |
| | HOP-62 | 24.18 |
| | HOP-92 | 44.42 |
| | NCI-H226 | 26.98 |
| | NCI-H23 | 30.70 |
| | NCI-H322M | 27.06 |
| | NCI-H460 | 2.83 |
| Colon Cancer | COLO 205 | 26.05 |
| | HCC-2998 | 25.98 |
| | HCT-116 | 20.87 |
| | HCT-15 | 34.01 |
| | HT29 | 31.44 |
| | KM12 | 29.83 |
| | SW-620 | 31.03 |

TABLE 4-continued

Compound: ART-Triazole-Sal

| Panel | Cell Line | Growth Percent |
|---|---|---|
| Breast Cancer | BT-549 | 40.56 |
| | HS 578T | 48.29 |
| | MCF7 | 13.62 |
| | MDA-MB-231/ATCC | 52.54 |
| | MDA-MB-435 | 35.26 |
| | NCI/ADR-RES | 15.88 |
| | T-47D | 37.45 |
| Ovarian Cancer | OVCAR-3 | 50.36 |
| | OVCAR-4 | 15.89 |
| | OVCAR-5 | 41.28 |
| | OVCAR-8 | 25.82 |
| | SK-OV-3 | 32.87 |
| Leukemia | CCRF-CEM | −14.86 |
| | HL-60(TB) | −31.16 |
| | K-562 | 17.31 |
| | MOLT-4 | −0.29 |
| | RPMI-8226 | 18.69 |
| | SR | 0.08 |
| Renal Cancer | 786-0 | 1.80 |
| | A498 | 50.94 |
| | ACHN | 15.69 |
| | CAKI-1 | 40.15 |
| | SN12C | 45.26 |
| | TK-10 | 38.15 |
| | UO-31 | −28.61 |
| Melanoma | LOX IMVI | 6.87 |
| | M14 | 3.07 |
| | MALME-3M | 42.33 |
| | SK-MEL-2 | −15.86 |
| | SK-MEL-28 | 27.59 |
| | SK-MEL-5 | 12.45 |
| | UACC-257 | 19.39 |
| | UACC-62 | 10.70 |
| Prostate Cancer | PC-3 | 38.28 |
| CNS Cancer | SF-268 | 21.15 |
| | SF-295 | 24.32 |
| | SF-539 | 14.19 |
| | SNB-19 | 45.73 |
| | SNB-75 | −8.40 |
| | U251 | 24.89 |

The mean growth percent for ART-Triazole-Sal is 22.31; the delta value is 53.47; and the range is 83.7.

TABLE 5

Compound: ART-Pyr-Sal

| Panel | Cell Line | Growth Percent |
|---|---|---|
| Non-Small Cell Lung Cancer | EKVX | 32.52 |
| | HOP-62 | 20.73 |
| | HOP-92 | 30.70 |
| | NCI-H226 | 1.83 |
| | NCI-H23 | 16.47 |
| | NCI-H322M | 31.89 |
| | NCI-H460 | 0.12 |
| | NCI-H522 | 10.19 |
| Colon Cancer | COLO 205 | 30.63 |
| | HCC-2998 | 4.91 |
| | HCT-116 | 18.34 |
| | HCT-15 | 21.89 |
| | HT29 | 29.61 |
| | KM12 | 29.31 |
| | SW-620 | 26.43 |
| Breast Cancer | BT-549 | 15.65 |
| | HS 578T | 19.38 |
| | MCF7 | 13.61 |
| | MDA-MB-231/ATCC | 50.08 |
| | MDA-MB-435 | 30.18 |
| | NCI/ADR-RES | 6.72 |
| | T-47D | 12.21 |

TABLE 5-continued

Compound: ART-Pyr-Sal

| Panel | Cell Line | Growth Percent |
|---|---|---|
| Ovarian Cancer | OVCAR-3 | 35.18 |
| | OVCAR-4 | 23.04 |
| | OVCAR-5 | 55.16 |
| | OVCAR-8 | 8.81 |
| | SK-OV-3 | 11.40 |
| Leukemia | CCRF-CEM | −17.26 |
| | HL-60(TB) | 5.22 |
| | K-562 | 26.88 |
| | MOLT-4 | 10.13 |
| | RPMI-8226 | 13.76 |
| | SR | −30.14 |
| Renal Cancer | 786-0 | −17.58 |
| | A498 | 5.27 |
| | ACHN | 10.64 |
| | CAKI-1 | 18.48 |
| | SN12C | 22.81 |
| | TK-10 | 31.03 |
| | UO-31 | 0.04 |
| Melanoma | LOX IMVI | 2.20 |
| | M14 | −9.91 |
| | MALME-3M | 8.61 |
| | SK-MEL-2 | −23.42 |
| | SK-MEL-28 | 29.92 |
| | SK-MEL-5 | −18.98 |
| | UACC-257 | 6.22 |
| | UACC-62 | 7.61 |
| Prostate Cancer | PC-3 | 21.62 |
| CNS Cancer | SF-268 | 12.40 |
| | SF-295 | 4.52 |
| | SF-539 | −29.69 |
| | SNB-19 | 20.71 |
| | SNB-75 | −6.97 |
| | U251 | 14.70 |

The mean growth percent for ART-Pyr-Sal is 12.83; the delta value is 42.97; and the range is 85.3.

TABLE 6

Compound: ART-Phe-Sal

| Panel | Cell Line | Growth Percent |
|---|---|---|
| Non-Small Cell Lung Cancer | EKVX | 28.62 |
| | HOP-62 | 12.31 |
| | HOP-92 | 56.27 |
| | NCI-H226 | 10.80 |
| | NCI-H23 | 31.01 |
| | NCI-H322M | 23.76 |
| | NCI-H460 | 0.59 |
| | NCI-H522 | 5.74 |
| Colon Cancer | COLO 205 | 26.59 |
| | HCC-2998 | 37.90 |
| | HCT-116 | 13.24 |
| | HCT-15 | 32.15 |
| | HT29 | 22.93 |
| | KM12 | 23.72 |
| | SW-620 | 30.24 |
| Breast Cancer | BT-549 | 25.29 |
| | HS 578T | 29.71 |
| | MCF7 | 12.70 |
| | MDA-MB-231/ATCC | 47.38 |
| | MDA-MB-435 | 15.04 |
| | NCI/ADR-RES | 21.55 |
| | T-47D | 34.12 |
| Ovarian Cancer | OVCAR-3 | 29.79 |
| | OVCAR-4 | 17.87 |
| | OVCAR-5 | 49.55 |
| | OVCAR-8 | 24.17 |
| | SK-OV-3 | 17.00 |

TABLE 6-continued

Compound: ART-Phe-Sal

| Panel | Cell Line | Growth Percent |
|---|---|---|
| Leukemia | CCRF-CEM | −19.45 |
| | HL-60(TB) | −54.70 |
| | K-562 | 8.87 |
| | MOLT-4 | −30.65 |
| | RPMI-8226 | 22.87 |
| | SR | −44.93 |
| Renal Cancer | 786-0 | −12.09 |
| | A498 | 0.33 |
| | ACHN | 10.40 |
| | CAKI-1 | 11.04 |
| | SN12C | 25.25 |
| | TK-10 | 20.96 |
| | UO-31 | −17.67 |
| Melanoma | LOX IMVI | 1.55 |
| | M14 | −37.45 |
| | MALME-3M | 16.70 |
| | SK-MEL-2 | −20.76 |
| | SK-MEL-28 | 22.75 |
| | SK-MEL-5 | −56.71 |
| | UACC-257 | 22.90 |
| | UACC-62 | −17.63 |
| Prostate Cancer | PC-3 | 31.46 |
| CNS Cancer | SF-268 | 10.84 |
| | SF-295 | −2.87 |
| | SF-539 | −18.69 |
| | SNB-19 | 27.53 |
| | SNB-75 | −16.75 |
| | U251 | 17.18 |

The mean growth percent for ART-Phe-Sal is 10.55; the delta value is 67.26; and the range is 112.98.

TABLE 7

Compound: ART-Phe-Pyridoxal

| Panel | Cell Line | Growth Percent |
|---|---|---|
| Non-Small Cell Lung Cancer | A549/ATCC | 26.36 |
| | EKVX | 12.34 |
| | HOP-62 | 20.25 |
| | HOP-92 | 20.97 |
| | NCI-H226 | 4.49 |
| | NCI-H23 | 13.86 |
| | NCI-H322M | 14.34 |
| | NCI-H460 | −3.33 |
| | NCI-H522 | 38.92 |
| Colon Cancer | COLO 205 | −4.40 |
| | HCC-2998 | 27.38 |
| | HCT-116 | 15.30 |
| | HCT-15 | 15.22 |
| | HT29 | 32.72 |
| | KM12 | 17.87 |
| | SW-620 | 14.32 |
| Breast Cancer | BT-549 | −18.57 |
| | HS 578T | −15.69 |
| | MCF7 | 1.55 |
| | MDA-MB-231/ATCC | 29.96 |
| | MDA-MB-435 | 18.74 |
| | NCI/ADR-RES | 44.16 |
| | T-47D | −2.71 |
| Ovarian Cancer | IGROV1 | 1.58 |
| | OVCAR-3 | 19.87 |
| | OVCAR-4 | 21.42 |
| | OVCAR-5 | 44.98 |
| | OVCAR-8 | 31.40 |
| | SK-OV-3 | −4.66 |
| Leukemia | CCRF-CEM | 2.34 |
| | HL-60(TB) | −4.98 |
| | K-562 | 22.86 |
| | MOLT-4 | −25.71 |
| | RPMI-8226 | 9.56 |
| | SR | −29.75 |

TABLE 7-continued

Compound: ART-Phe-Pyridoxal

| Panel | Cell Line | Growth Percent |
|---|---|---|
| Renal Cancer | 786-0 | −19.54 |
| | A498 | −36.78 |
| | ACHN | 7.45 |
| | CAKI-1 | −12.33 |
| | RXF 393 | 35.07 |
| | SN12C | 16.82 |
| | TK-10 | 6.35 |
| | UO-31 | 4.39 |
| Melanoma | LOX IMVI | 4.22 |
| | MALME-3M | −17.79 |
| | SK-MEL-2 | 20.14 |
| | SK-MEL-28 | −7.02 |
| | SK-MEL-5 | −43.83 |
| | UACC-257 | 1.40 |
| | UACC-62 | −8.10 |
| Prostate Cancer | DU-145 | −9.65 |
| | PC-3 | 31.12 |
| CNS Cancer | SF-268 | 1.39 |
| | SF-295 | 25.08 |
| | SF-539 | −20.49 |
| | SNB-19 | 4.26 |
| | SNB-75 | 42.44 |
| | U251 | 17.87 |

The mean growth percent for ART-Phe-Pyridoxal is 7.85; the delta value is 51.68; and the range is 88.81.

With the exception of ART-Triazole-Sal, the mean growth percent for each compound was less than 20%. The lowest mean growth percent was observed with ART-Furan-Sal, at 6.1%; next was ART-Phe-Pyridoxal, at 7.85%. Of the six compounds, the highest mean growth percent was observed with ART-Triazole-Sal, at 22.31%.

While illustrative embodiments have been illustrated and described, it will be appreciated that various changes can be made therein without departing from the spirit and scope of the invention.

The invention claimed is:

1. A compound having the formula (I):

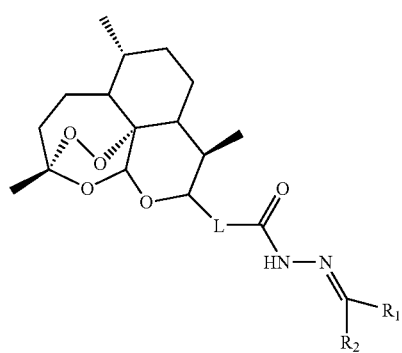

(I)

wherein L is —R—, or —O—R—, and R is selected from the group consisting of:
(a) substituted or unsubstituted arylene;
(b) substituted or unsubstituted heteroarylene;
(c) substituted or unsubstituted alkylene;
(d) substituted or unsubstituted alkenylene; and
(e) substituted or unsubstituted alkynylene;

$R_1$ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and $R_2$ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

2. The compound of claim 1, wherein L is —O—R— and R is a substituted or unsubstituted alkylarylene.

3. The compound of claim 1, wherein L is —O—R— and R is a substituted or unsubstituted alkylheteroarylene.

4. The compound of claim 1, wherein L is —O—R— and R is selected from a group consisting of

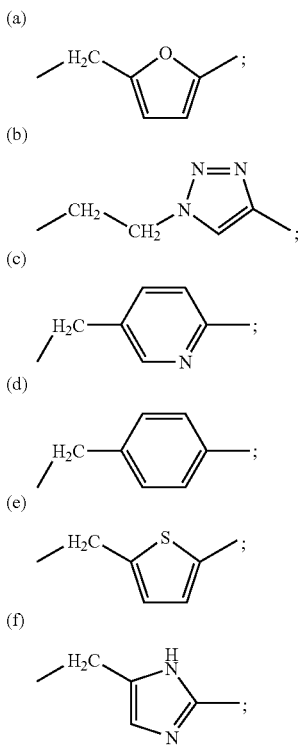

(g) —$(CH_2)_m$—, wherein m is an integer from 1 to 10; and
(i) —$(CH_2—CH_2)_n$—O—$(CH_2)_o$—, wherein n is an integer from 1 to 10 and o is an integer from 1 to 10.

5. The compound of claim 1, wherein L is R, and R is selected from a group consisting of:
(a) —$(CH_2)_m$—, wherein m is an integer from 1 to 10; and
(b) —$(CH_2—CH_2)_n$—O—$(CH_2)_o$—, wherein n is an integer from 1 to 10 and o is an integer from 1 to 10.

6. The compound of claim 1, wherein $R_1$ is hydrogen.

7. The compound of claim 1, wherein $R_2$ is selected from a group consisting of:
(a) phenyl;
(b) 2-hydroxy phenyl;
(c) 2-methyl-3-hydroxymethyl-5-hydroxy-4-pyridyl;
(d) 2-hydroxy-1-naphthyl;
(e) 2-hydroxy-pyridyl;
(f) 2-hydroxy-furanyl;
(g) 2-hydroxy-thiofuranyl; and
(h) 4-hydroxyl-imidazolyl.

8. A compound having the formula (II):

(II)

wherein $R_1$ is selected from the group consisting of:
  (a) hydrogen;
  (b) substituted or unsubstituted alkyl;
  (c) substituted or unsubstituted alkenyl;
  (d) substituted or unsubstituted alkynyl;
  (e) substituted or unsubstituted aryl; and
  (f) substituted or unsubstituted heteroaryl;
$R_2$ is selected from the group consisting of:
  (a) substituted or unsubstituted alkyl;
  (b) substituted or unsubstituted alkenyl;
  (c) substituted or unsubstituted alkynyl;
  (d) substituted or unsubstituted aryl; and
  (e) substituted or unsubstituted heteroaryl;
$R_3$ is selected from a group consisting of:
  (a) substituted or unsubstituted alkylene;
  (b) substituted or unsubstituted alkenylene; and
  (c) substituted or unsubstituted alkynylene; and
Ar is selected from the group consisting of:
  (a) substituted or unsubstituted arylene; and
  (b) substituted or unsubstituted heteroarylene.

9. The compound of claim 8, wherein $R_1$ is hydrogen.

10. The compound of claim 8, wherein $R_2$ is a substituted or unsubstituted aryl.

11. The compound of claim 8, wherein $R_2$ is selected from a group consisting of
  (a) phenyl;
  (b) 2-hydroxy phenyl; and
  (c) 2-methyl-3-hydroxymethyl-5-hydroxy-4-pyridyl.

12. The compound of claim 8, wherein $R_3$ is methylene or ethylene.

13. The compound of claim 8, wherein Ar is selected from the group consisting of:

(a)

(b)

(c)

(d)

(e)

(f)

(g)

(h) ; and (i)

wherein $R_4$ at each position is independently selected from a group consisting of
  (a) hydrogen;
  (b) substituted or unsubstituted alkyl;
  (c) substituted or unsubstituted alkenyl;
  (d) substituted or unsubstituted alkynyl;
  (e) substituted or unsubstituted aryl;
  (f) hydroxy;
  (g) alkoxy;
  (h) dialkylamino;
  (i) thio;
  (j) alkylthio;
  (k) carboxyl;
  (l) carboxyamide;
  (m) carboxyester;
  (n) nitrile;
  (o) halogen; and
  (p) nitro.

14. A compound having the formula (III):

(III)

wherein L is a linker comprising one or more groups selected from the group consisting of:
(a) substituted or unsubstituted arylene;
(b) substituted or unsubstituted heteroarylene;
(c) substituted or unsubstituted alkylene;
(d) substituted or unsubstituted alkenylene; and
(e) substituted or unsubstituted alkynylene;

$R_1$ is selected from the group consisting of:
(a) hydrogen;
(b) substituted or unsubstituted alkyl;
(c) substituted or unsubstituted aryl;
(d) substituted or unsubstituted heteroaryl;
(e) substituted or unsubstituted alkenyl; and
(f) substituted or unsubstituted alkynyl; and $R_2$ is selected from the group consisting of:
(a) substituted or unsubstituted alkyl;
(b) substituted or unsubstituted aryl;
(c) substituted or unsubstituted heteroaryl;
(d) substituted or unsubstituted alkenyl; and
(e) substituted or unsubstituted alkynyl.

15. The compound of claim 14, wherein L is —CH$_2$—CH—CH$_2$—.

16. The compound of claim 14, wherein $R_1$ is hydrogen.

17. The compound of claim 14, wherein $R_2$ is substituted or unsubstituted aryl.

18. A compound selected from the group consisting of:
(a) N'-(2-hydroxybenzylidene)-5-(dihydroxyartemisinin-methyl)-furan-2-carbohydrazide;
(b) N'-(2-hydroxybenzylidene)-1-(dihydroxyartemisinin-ethyl)-1H-1,2,3-triazole-4-carbohydrazide;
(c) N'-(2-hydroxybenzylidene)-5-(dihydroxyartemisinin-methyl)-2-pyridine carbohydrazide;
(d) N'-(2-hydroxybenzylidene)-4-(dihydroxyartemisinin-methyl)-phenyl carbohydrazide;
(e) N'-(benzylidene)-4-(dihydroxyartemisinin-methyl)-phenyl carbohydrazide;
N'-(5-hydroxy-3-hydroxymethyl-2-methyl-4-pyridylidene)-4-(dihydroxyartemisinin-methyl)-phenyl carbohydrazide;
(f) N'-(2-hydroxybenzylidene)-(2E)-4-(dihydroartemisin-methyl)-2-butenoic hydrazide; and
(g) N'-(2-hydroxybenzylidene)-4-(dihydroartemisin-methyl)-2-butynoic hydrazide.

19. A composition comprising a compound of anyone of claims 1, 8, 14 and 18 and a pharmaceutically acceptable carrier.

* * * * *